US007339159B2

(12) United States Patent
Juh et al.

(10) Patent No.: US 7,339,159 B2
(45) Date of Patent: Mar. 4, 2008

(54) PHANTOM FOR EVALUATING ACCURACY OF IMAGE REGISTRATION SOFTWARE

(75) Inventors: Ra Hyeong Juh, Seoul (KR); Ho Sang Jin, Iksan (KR); Joo Young Song, Gwangju (KR); Tae Suk Suh, Seoul (KR); Bo Young Choe, Seoul (KR); Hyoung Koo Lee, Seoul (KR)

(73) Assignee: Ra Hyeong Juh, Ho Sang Jin, Joo Young Song, Tae Suk Suh, and Catholic University of Medical College (KR)

( * ) Notice: Subject to any disclaimer, the term of this patent is extended or adjusted under 35 U.S.C. 154(b) by 695 days.

(21) Appl. No.: 10/840,929

(22) Filed: May 7, 2004

(65) Prior Publication Data

US 2005/0008126 A1 Jan. 13, 2005

(30) Foreign Application Priority Data

May 9, 2003 (KR) ..................... 10-2003-0029296

(51) Int. Cl.
*G01D 18/00* (2006.01)

(52) U.S. Cl. .................................... 250/252.1; 378/207

(58) Field of Classification Search ............ 250/252.1; 378/207

See application file for complete search history.

(56) References Cited

U.S. PATENT DOCUMENTS

| | | | | |
|---|---|---|---|---|
| 4,499,375 | A * | 2/1985 | Jaszczak | 250/252.1 |
| 4,692,704 | A * | 9/1987 | Gray | 324/318 |
| 4,777,442 | A * | 10/1988 | Rosenthal | 324/318 |
| 4,818,943 | A * | 4/1989 | Chandra | 324/318 |
| 5,036,280 | A * | 7/1991 | Chesavage | 324/308 |
| 5,793,835 | A * | 8/1998 | Blanck | 378/4 |
| 6,207,952 | B1 * | 3/2001 | Kan et al. | 250/252.1 |
| 2005/0123178 | A1 * | 6/2005 | Teppaz et al. | 382/128 |

* cited by examiner

*Primary Examiner*—David Porta
*Assistant Examiner*—Mark R Gaworecki
(74) *Attorney, Agent, or Firm*—Thelen Reid Brown Raysman and Steiner LLP

(57) ABSTRACT

Provided is a phantom for evaluating the accuracy of image registration software based on a result of matching tomograms of a predetermined position of the phantom, taken using two or more imaging apparatuses. Accordingly, it is possible to more efficiently evaluate the accuracy of the image registration software by comparing the tomograms with one another using a three-dimensional analysis. In addition, it is possible to facilitate the comparison of the tomograms with one another by installing a plurality of indicating bars in the phantom so that their cross sections can appear on each of the tomograms.

10 Claims, 21 Drawing Sheets

21b 21a 21 11 19d 19c 19b 19 Z 17 15b 15 19p 16 15d 19a 15a 15e 15c 13c 13 13b 13a

PHANTOM FOR EVALUATING ACCURACY OF IMAGE REGISTRATION SOFTWARE

BACKGROUND OF THE INVENTION

This application claims the priority of Korean Patent Application No. 2003-29296, filed on May 9, 2003, in the Korean Intellectual Property Office, the disclosure of which is incorporated herein in its entirety by reference.

1. Field of the Invention

The present invention relates to a phantom that can be tomographed by various medical imaging apparatuses after being built in each of the medical imaging apparatuses, and more particularly, to a phantom for evaluating accuracy of image registration software by matching and comparing images, taken by various medical imaging apparatuses, with one another with the use of imaging registration software.

2. Description of the Related Art

Recent developments in medical science and technology have enabled many medical procedures and diagnoses that at one time were considered impossible. One of these developments is imaging apparatuses, such as a computed tomography (CT) apparatus, a magnetic resonance imaging (MRI) apparatus, a single photon emission computed tomography (SPECT) apparatus, and a positron emission tomography (PET) apparatus, which enable a detailed observation of the entire human body, and thus is very important for diagnosing or treating diseases such as tumors or cancer.

Since the CT, MRI, SPECT, and PET apparatuses are based on different imaging principles and have different advantages and disadvantages, it is preferable to use the one that best fits the purpose of diagnosis.

The CT apparatus is an imaging apparatus that uses differences in X-ray attenuation coefficients among parts of, for example, the entire human body, which are caused by electron density variations. The CT apparatus can provide detailed anatomical images with fewer distortions. In particular, the CT apparatus provides excellent imaging of a bone structure of the entire human body. In addition, the CT apparatus allows electron density information to be immediately applied to dose calculations, and thus can provide standard images for the planning of radioactive treatments.

The MRI apparatus is an imaging apparatus that uses frequency conversion signals generated in the process of magnetizing and demagnetizing hydrogen atoms in the entire human body. The MRI apparatus provides anatomical images with high contrast and high resolution. However, there is a possibility of the MRI apparatus providing distorted images, which is mainly due to the irregularity of magnetic fields.

The SPECT apparatus is an imaging apparatus that forms images of parts of the entire human body by injecting a reagent containing radionuclides that emit gamma rays into a desired part of the entire human body and detecting the gamma rays emitted from the radionuclides. The SPECT apparatus is generally used for analyzing metabolism and nervous functions of the desired part of the entire human body. However, the SPECT apparatus provides images with relatively low resolution, so it is rather difficult to obtain detailed anatomical information from SPECT images.

The PET apparatus forms images of parts of the entire human body using the fact that a malignant tumor in the entire human body consumes more glucose than normal tissues. The PET apparatus makes it possible to provide early diagnosis of abnormal symptoms or diseases by visualizing degrees of sugar, oxygen, and protein metabolism in the entire human body. However, the PET apparatus cannot provide detailed information on, for example, where a tumor is located in the entire human body and how big the tumor is.

The above-described imaging apparatuses have different advantages and disadvantages. Therefore, for more accurate and more effective diagnosis and treatment of diseases, it would be desirable to get an image of a desired part of the entire human body using as many imaging apparatuses as possible and analyze the resultant images taken by the different imaging apparatuses by comparing them with one another.

For a more accurate comparative analysis of images taken by different imaging apparatuses, image registration, which is a technique of mapping the images on the same coordinate system, is necessary. The image registration operation indicates processes of mapping and overlapping various images of a desired part of the entire human body, taken by the different imaging apparatuses, on a given coordinate system, thus guaranteeing more accurate and more effective diagnosis and treatment of diseases.

An image registration tool, namely, image registration software, matches images of a desired portion of the entire human body, taken by different imaging apparatuses, with one another. Therefore, unless accuracy of the image registration software is guaranteed, reliability of image registration results cannot be attained. Inaccurate image registration results inevitably lead to inaccurate diagnosis and inappropriate treatment of diseases.

Therefore, research has been carried out on image registration, and development of image registration software that can provide very accurate image registration results in a more convenient manner is under way.

In the meantime, a phantom is necessary for evaluating the general performance and accuracy of the image registration software. The phantom makes it possible to obtain multiple images and more accurately carry out error analysis. In short, the phantom can be tomographed using various imaging apparatuses and are used for evaluating the accuracy of the image registration software and other necessary procedures.

Until now, no phantoms have been developed exclusively for evaluating the accuracy of image registration software. In other words, conventional phantoms have been mainly used to control the quality of imaging apparatuses or radioactive therapy equipment so that they can compare images at best two-dimensionally.

SUMMARY OF THE INVENTION

The present invention provides a phantom for evaluating the accuracy of image registration software. The phantom is used for evaluating the accuracy of the image registration software by allowing a three-dimensional comparison of images taken using different medical imaging apparatuses. A plurality of indicating bars are included in the phantom such that their cross sections can appear on each of the images, thus facilitating the comparison of the images and the evaluation of the image registration software.

According to an aspect of the present invention, there is provided a phantom for evaluating the accuracy of image registration software based on a result of matching tomograms of a predetermined position of the phantom taken using two or more imaging apparatuses. The phantom includes a container, which can contain water therein; and a phantom main body, which is installed in the container, the phantom main body having an empty space therein that embodies a predetermined portion of the entire human body, the empty space being able to be filled with water.

The phantom may further include a localizer, which is disposed between the phantom main body and an inner sidewall of the container and indicates the height in the axial direction of the phantom to which the tomograms correspond.

The phantom main body may include a case, which can contain water therein; and a slice stack, which comprises a plurality of unit slices that are sequentially stacked in the case and has an empty space that embodies the predetermined portion of the entire human body.

The unit slices may be plates with a predetermined thickness, stacked on a bottom surface of the case, holes may be formed in each of the unit slices so that they can represent cross sections of the predetermined portion of the entire human body, and the empty space inside the slice stack may be defined by the holes in each of the unit slices when the unit slices are stacked.

The phantom may further include at least one vertical indicating bar, which extends vertically upward from a bottom surface of the container such that its cross section appears on each of the tomograms of the phantom.

The localizer may include a frame, which comprises a main body, which has a cylindrical shape with a predetermined height and contains the phantom main body therein, and upper and lower rings, which have a predetermined width and are respectively fixed to upper and lower ends of the main body; and at least one N-shaped indicator, which is coupled to the upper and lower rings at both the upper and lower ends such that its cross section appears on each of the tomograms of the phantom, the at least one N-shaped indicator comprising three indicating bars, two of which extend vertically upward from the lower ring and are separated by a predetermined distance, and one of which is slanted between the two indicating bars such that its lower end is located in the vicinity of the lower end of one of the two indicating bars disposed vertically and its upper end is located in the vicinity of the lower end of the other indicating bar disposed vertically.

At least two N-shaped indicators may be evenly distributed around the circumference of the phantom main body.

Each of the indicating bars may include an acrylic tube, which is fixed to the upper and lower rings at both ends and has an empty space therein; and an inserting rod, which is disposed in the acrylic tube such that its cross section appears on each of the tomograms of the phantom.

The phantom main body may include a slice stack, which comprises a plurality of unit slices that are sequentially stacked in the case and has an empty space therein that embodies the predetermined portion of the entire human body; and at least one indicating bar, which is vertically fixed between the slice stack and the inner sidewall of the container such that its cross section can appear in each of the tomograms of the phantom.

The at least one indicating bar may include an acrylic tube, which has an empty space therein; and an inserting rod, which is disposed in the acrylic tube such that its cross section appears on each of the tomograms of the phantom.

The unit slices may be plates with a predetermined thickness, which are stacked on a bottom surface of the case, holes may be formed in each of the unit slices so that they can represent a cross section of the predetermined portion of the entire human body, and the empty space inside the slice stack may be defined by the holes in each of the unit slices when the unit slices are stacked.

The phantom main body may have at least one auxiliary hole vertically formed through therethrough.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

A phantom for evaluating the accuracy of image registration software according to the present invention is formed of acrylic resin. Acrylic resin rods or lead rods may be selectively used as inserting rods 17*b*, 32*b*, and 57*d* of the phantom depending on the kind of imaging apparatus. Here, the acrylic resin can be polymethylacrylate, polymethylmetacrylate, a mixture thereof, a copolymer of methylacrylate or methylmetacrylate.

Figure 1:
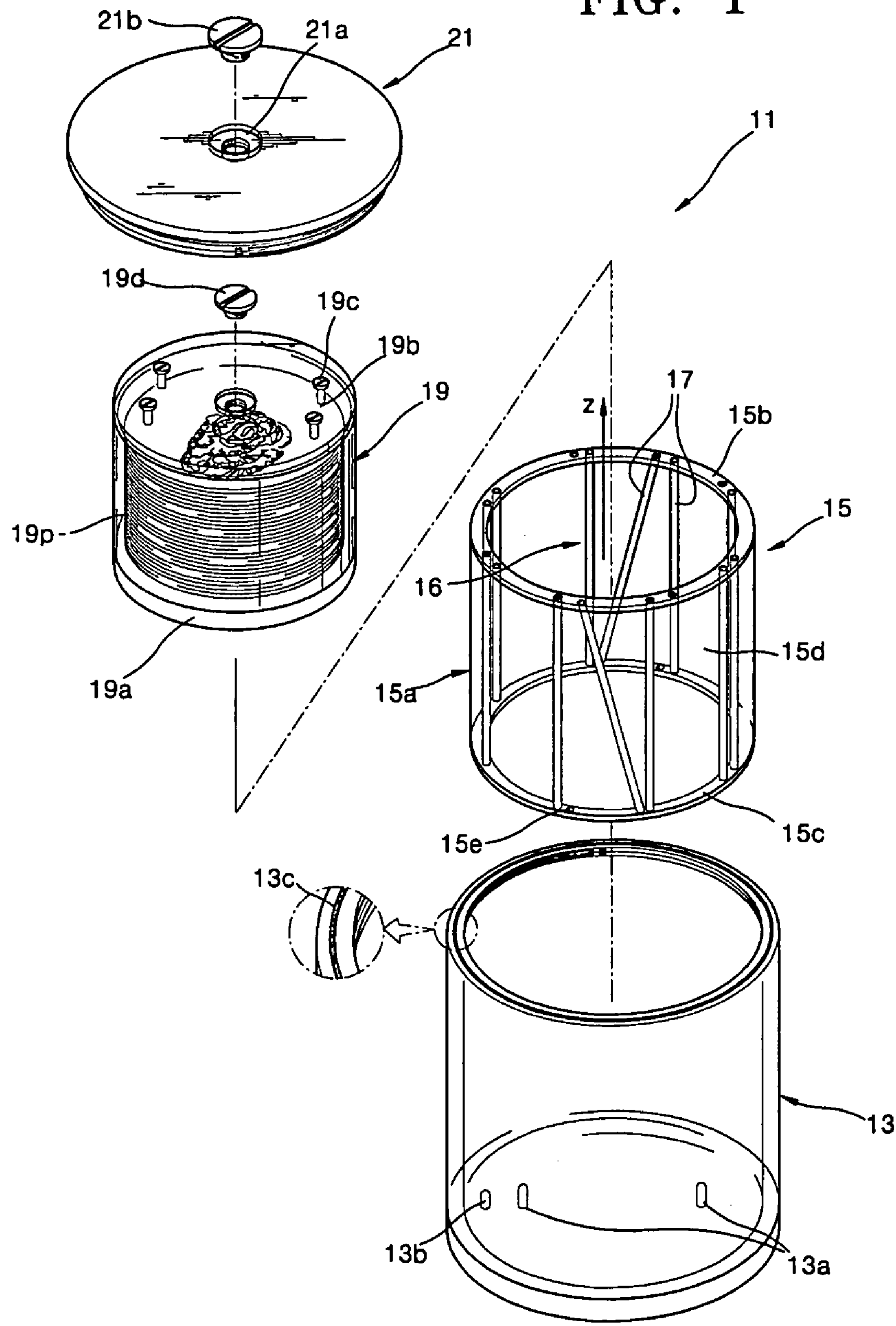
FIG. 1 is an exploded perspective view of a phantom for evaluating accuracy of image registration software according to a first embodiment of the present invention.

FIG. 1 is an exploded perspective view of a phantom 11 for evaluating the accuracy of image registration software according to a first embodiment of the present invention. Referring to FIG. 1, the phantom 11 includes a container 13, which can contain water therein, a localizer 15, which has an empty space therein and is inserted into the container 13 such that the outer surface of the localizer 15 contacts the inner surface of the container 13, a phantom main body 19, which is inserted into the empty space of the localizer 15, and a lid 21, which hermetically seals the container 13 with the localizer 15 and the phantom main body 19 contained in the container 13.

The container 13 is cylindrical with a predetermined capacity. Supporting protrusions 13*a* and 13*b* are formed on the bottom surface of the container 13. The supporting protrusion 13*b*, which is located closer to the inner sidewall of the container 13 than the supporting protrusions 13*a*, is fitted into a hole 15*e* formed in a lower ring 15*c* of the localizer 15, and the supporting protrusions 13*a* are fitted into two holes (19*k* of FIG. 3), respectively, formed at the bottom of the phantom main body 19. The supporting protrusions 13*a* and 13*b* serve as stoppers that prevent the localizer 15 and the phantom main body 19 from undesirably moving in the container 13.

An O-ring 13*c* is disposed on top of the container 13 along the circumference of the container 13. The O-ring 13*c* prevents water contained in the container 13 from leaking.

The localizer 15 comprises a frame 15*a* and four N-shaped indicators 16. The frame 15*a* comprises a main body 15*d*, which is cylindrical and contacts the inner sidewall of the container 13, and upper and lower rings 15*b* and 15*c*, which are fixed to upper and lower ends, respectively, of the main body 15*d*. The upper and lower rings 15*b* and 15*c* have the same width. An outer edge of each of the upper and lower rings 15*b* and 15*c* is fixed to the main body 15*d* so that the upper and lower rings 15*b* and 15*c* and the main body 15*d* form an empty space within.

An upper end of each of the N-shaped indicators 16 is coupled with the upper ring 15*b*, and a lower end of each of the N-shaped indicators 16 is coupled with the lower ring 15*c*. Therefore, the N-shaped indicators 16 connect the upper and lower rings 15*b* and 15*c*. The N-shaped indicators 16 are evenly distributed around the circumference of the localizer 15. Each of the N-shaped indicators 16 comprises three indicating bars 17 forming an alphabet N. Each of the indicating bars 17 is represented by a point on an image of the phantom 11, taken by an imaging apparatus, which will be described in greater detail later.

Two of the three indicating bars 17 of each of the N-shaped indicators 16 extend vertically from the lower ring (15*c*) to connect the upper and lower rings 15*b* and 15*c*, and the other indicating bar 17 is slanted between the two vertical indicating bars 17. In other words, one end of the slanted indicating bar 17 between the two vertical indicating bars 17 is fixed to the upper ring 15*b* in the vicinity of one of the two vertical indicating bars 17, and the other end of the slanted indicating bar 17 between the two vertical indicating bars 17 is fixed to the lower ring 15*c* in the vicinity of the other vertical indicating bar 17.

Therefore, when taking several horizontal tomograms of the phantom 11 along a Z direction, namely, along the axial direction of the phantom 1, each tomograms have different distance patterns of point from one another according to the height of axial direction. In other words, the cross-sectional view of each of the N-shape indicators 16 varies from position to position along the axial direction of the phantom 11, so the height of axial direction can be known based on the point distance pattern of each of the horizontal tomograms, which will be described in greater detail later with reference to FIG. 7.

The phantom main body 19 is installed in the empty space of the localizer 15 such that the outer circumference of the phantom main body 19 contacts the inner circumference of each of the upper and lower rings 15*b* and 15*c*. The phantom main body 19 comprises a cylindrical case 19*a*, which can contain water, a slice stack 19*p*, which is disposed in the cylindrical case 19*a*, and a sealing cover 19*b*, which hermetically seals the cylindrical case 19*a*.

The slice stack 19*p* includes a plurality of unit slices (19*q* of FIG. 3), which are disk-shaped. The slice stack 19*p* has an empty space copying a certain part of the entire human body, for example, an internal organ or the brain. In the present embodiment, the empty space of the slice stack 19 embodies the brain.

An opening/shutting screw 19*d*, which opens or shuts a water supply hole (19*v* of FIG. 3), is disposed at the center of the sealing cover 19*b*.

A water supply hole 21*a* is formed in the middle of the lid 21. The water supply hole 21*a* is opened or closed by the opening/shutting screw 21*b*. When the water supply holes 21*a* and 19*v* are opened, the empty space of slice stack 19*p* can be filled with water supplied thereinto.

Figure 2:
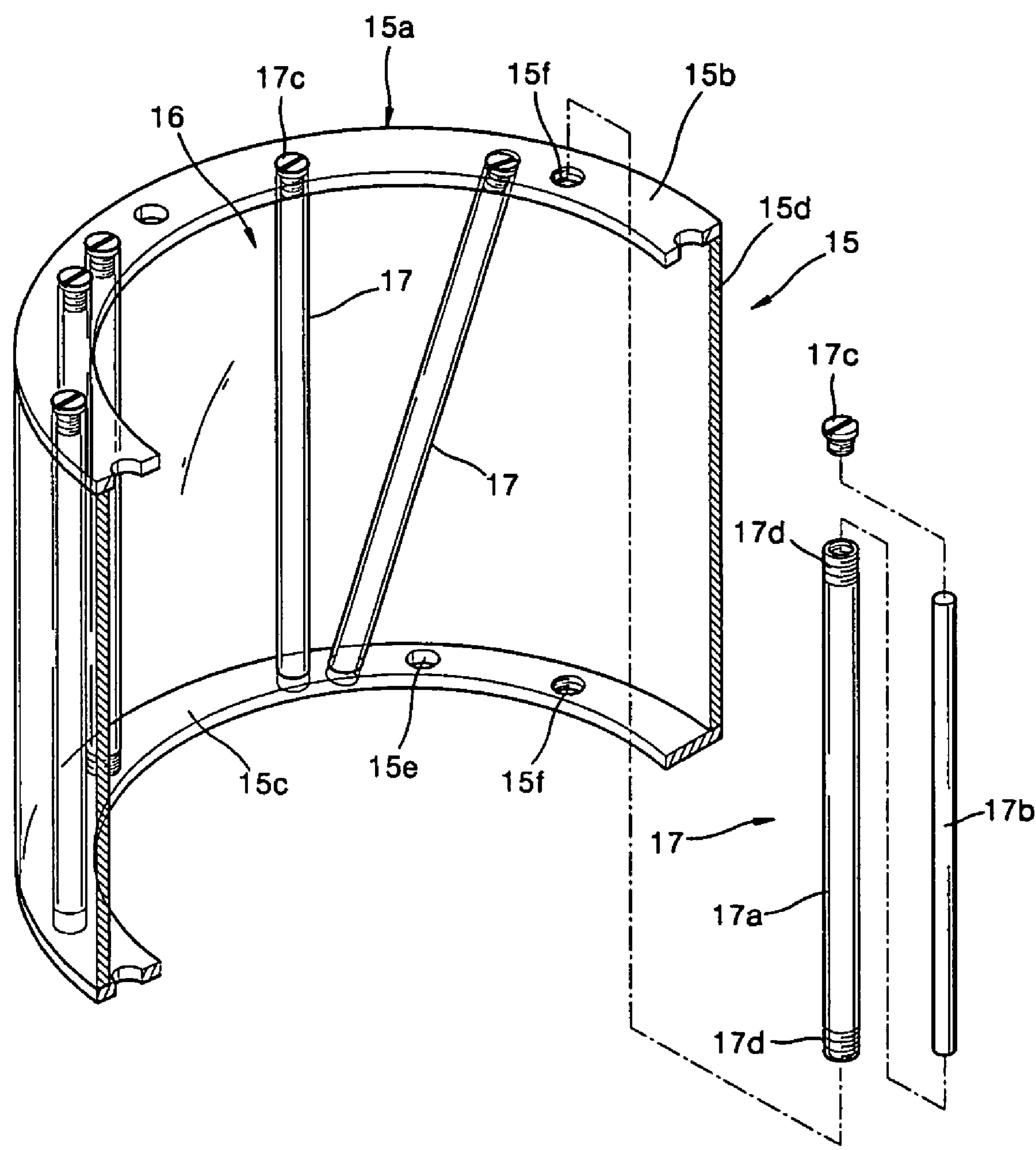
FIG. 2 is a cutaway view of a localizer of FIG. 1.

FIG. 2 is a cutaway view of the localizer 15 of FIG. 1. Referring to FIG. 2, the localizer 15 includes the main body 15*d*, which is cylindrical, and the upper and lower rings 15*b* and 15*c*, which are fixed to the upper and lower ends, respectively, of the main body 15*d*. The upper and lower rings 15*b* and 15*c* each have a predetermined width and a predetermined thickness. Each of the upper and lower rings 15*b* and 15*c* has female screw holes 15*f* such that the N-shaped indicators 16 can be fixed into the female screw holes 15*f*.

As described above, each of the N-shaped indicators 16 includes three indicating bars 17.

Each of the indicating bars 17 includes an acrylic tube 17*a*, an inserting rod 17*b*, which is inserted into the acrylic tube 17*a*, and a sealing screw 17*c*, which hermetically seals an upper end of the acrylic tube 17*a*.

Male threads are formed along the outer circumference of either end of the acrylic tube 17*a* so that the acrylic tube 17*a* can be fitted into female screw holes 15*f*. The acrylic tube

17*a* contains the inserting rod 17*b* such that a cross section of the inserting rod 17*b* can be displayed on an image of the phantom 11 taken by an imaging apparatus. The upper end of the acrylic tube 17*a* is open and can be hermetically sealed by the sealing screw 17*c*. Therefore, if necessary, the inserting rod 17*b* can be removed from the acrylic tube 17*a*, and then other inserting rod can be inserted into the acrylic tube 17*a*.

The inserting rod 17*b* is a rod with a predetermined diameter. An acrylic rod or a lead rod could be used as the inserting rod 17*b* depending on the type of imaging apparatus. For example, when taking an image of the phantom 11 using a CT apparatus or an MRI apparatus, an acrylic rod is used as the inserting rod 17*b*. On the other hand, when taking the image of the phantom 11 using a SPECT apparatus or a PET apparatus, a lead rod is used as the inserting rod 17*b* because an acrylic rod shot by the SPECT or PET apparatus does not appear on the tomogram of the phantom 11.

Figure 3:
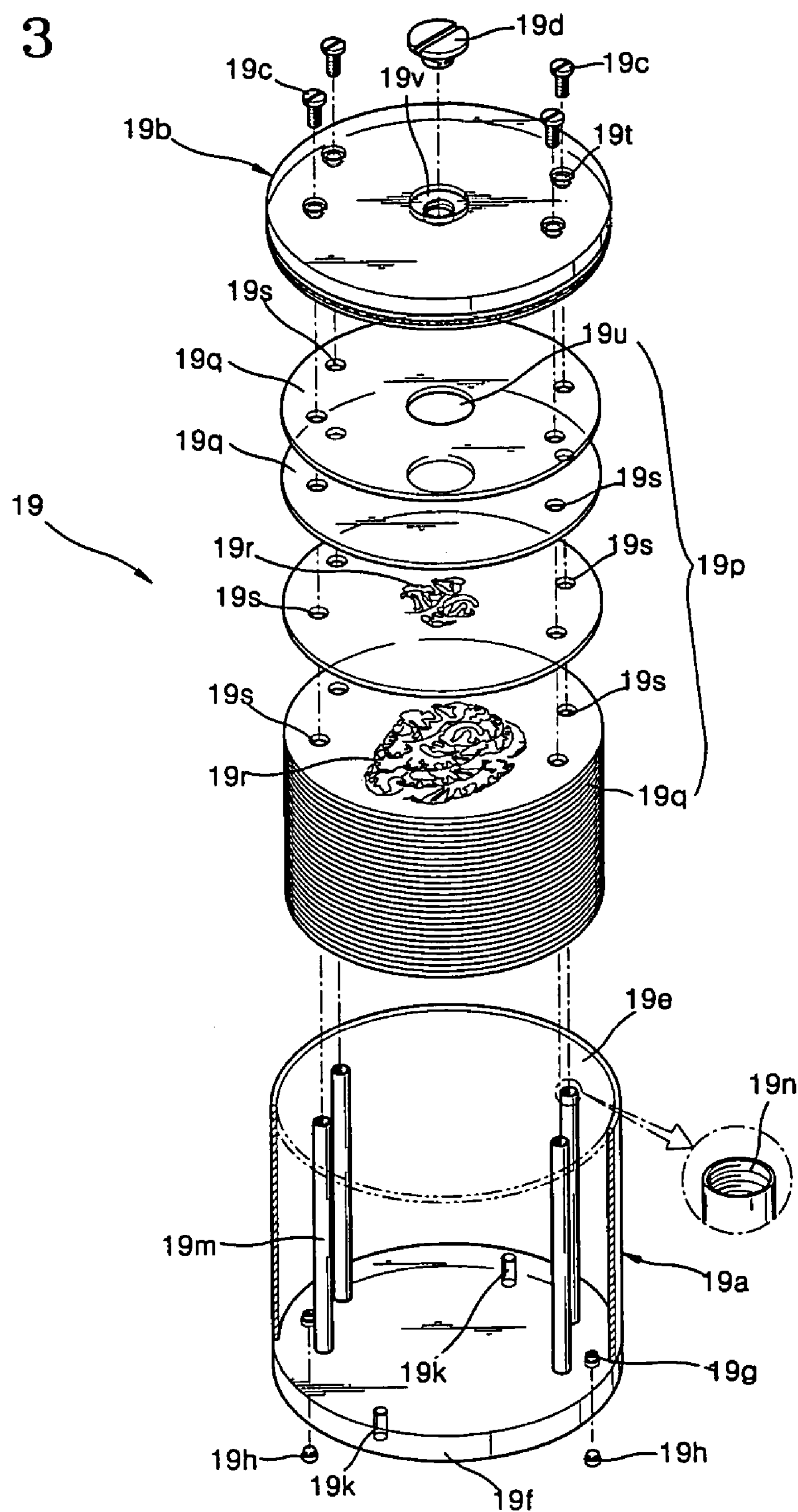
FIG. 3 is an exploded perspective view of a main body of the phantom of FIG. 1.

FIG. 3 is an exploded perspective view of the phantom main body 19 of FIG. 1. Referring to FIG. 3, the cylindrical case 19*a* of the phantom main body 19 includes a bottom plate 19*f*, which is circular, and a sidewall 19*e*, which is cylindrical and is firmly fixed to the bottom plate 19*f*.

Two opening holes 19*g* are formed in the bottom plate 19*f* together with the holes 19*k*. The opening holes 19*g* can be hermetically sealed by an opening/shutting screw 19*h*. Water contained in the phantom main body 19 can be quickly discharged through the opening holes 19*g*.

Four vertical supporting rods 19*m* are fixed to the bottom plate 19*f*. The vertical supporting rods 19*m* have equal diameters and lengths and are perpendicular to the top surface of the bottom plate 19*f*. Female screws 19*n* are formed with threads on the interior surface of an upper portion of each of the vertical supporting rods 19*m*. Once the vertical supporting rods 19*m* are fitted into the slice stack 19*p*, their upper portions protrude over the slice stack 19*p*. Fixing bolts 19*c* are fitted into the female screws 19*n* passing through the sealing cover 19*b*.

As described above, the slice stack 19*p*, which is disposed in the case 19*a*, comprises the unit slices 19*q* that are sequentially stacked. Each of the unit slices 19*q* is disk-shaped. And an empty space is formed in the slice stack 19*q*, copying shape of the brain. The empty space inside the slice stack 19*p* can be exposed to the outside so that it can be filled with water supplied into the slice stack 19*p* from the outside.

Four through holes 19*s* are formed through the slice stack 19*p*. The unit slices 19*q* can be neatly arranged in the cylindrical case 19*a* due to the four vertical supporting rods 19*m*, which pass through the four through holes 19*s*, respectively.

Brain section holes 19*r* are formed in a central portion of each of the unit slices 19*q* such that they represent a shape of brain. More specifically, the brain section holes 19*r* are formed by referring to tomograms of different positions of the read brain, which are taken at predetermined intervals along the axial direction.

When the four vertical supporting rods 19*m* are fitted into each of the unit slices 19*q* through the four through holes 19*s*, respectively, empty spaces, which embody the entire brain, are defined by the brain section holes 19*r* of each of the unit slices 19*q*. The slice stack 19*p* can be filled with water supplied thereinto such that the shape of the brain embodied by the empty spaces is filled with water.

First two unit slices 19*q* of the top of the slice stack 19*p* are provided so that the bottom surface of the sealing cover 19*b* and the unit slice 19*q* can be separated from each other. Since the first two unit slices 19*q* from the top of the slice stack 19*p* have a through hole 19*u* in their centers, they do not interfere with the flow of water supplied into the slice stack 19*p*.

The water supply hole 19*v*, which can be sealed by the opening/shutting screw 19*d*, is formed in the center of the sealing cover 19*b*, and four bolt holes 19*t* are formed around the water supply hole 19*v*. The fixing bolts 19*c* are fitted into the female screws 19*n*, passing through the four bolt holes 19*t*.

Figure 4:
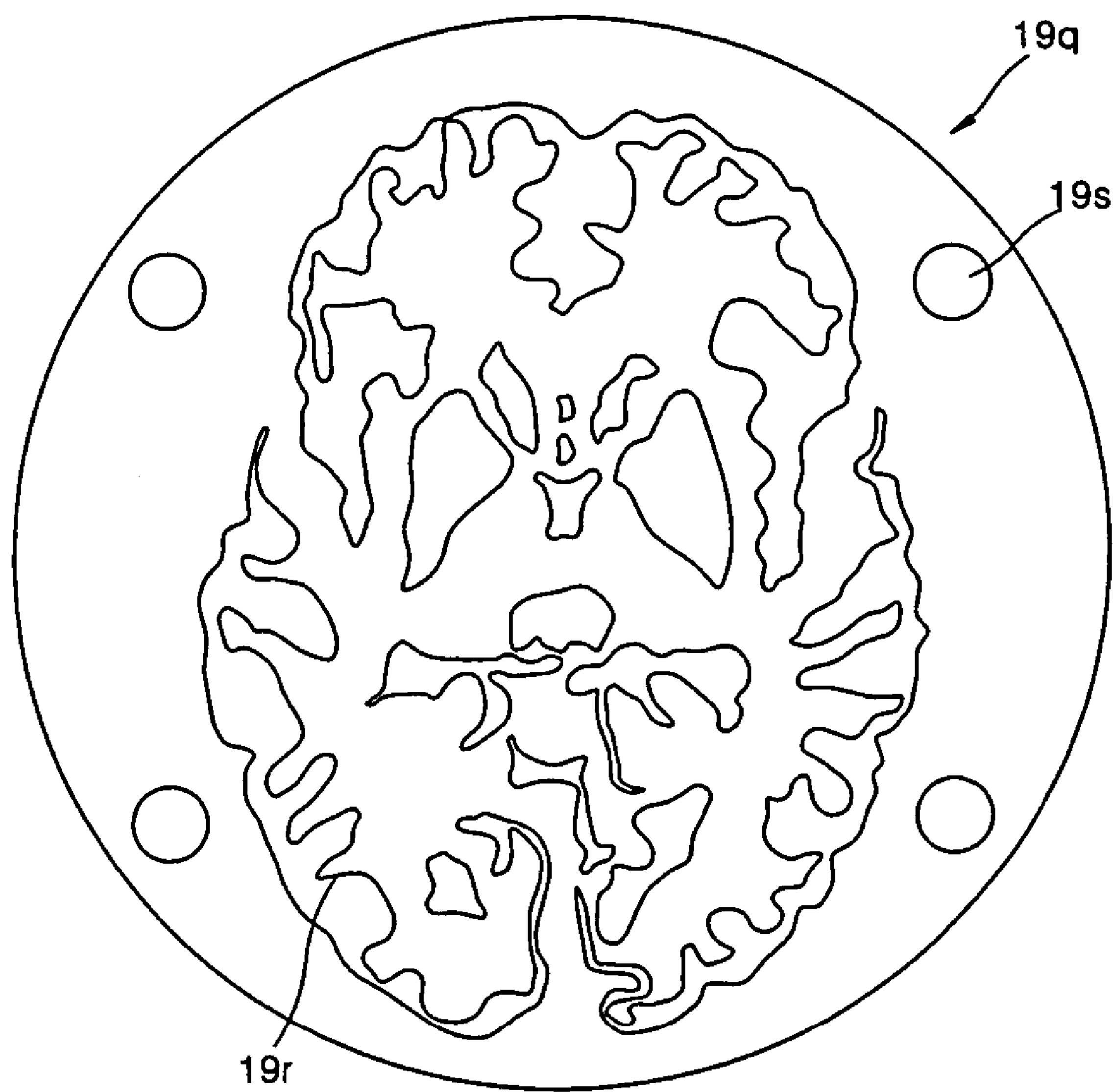
FIG. 4 is a plan view of one of a plurality of unit slices of the main body of FIG. 3.

FIG. 4 is a plan view of one of the unit slices 19*q* of the slice stack 19*p* of FIG. 3. Referring to FIG. 4, four through holes 19*s* are disposed a predetermined distance from the outer boundary of a unit slice 19*q*, and the brain section hole 19*r* is formed through the unit slice 19*q*. The brain section hole 19*r* embodies a cross section at a predetermined position of the brain. Cross sections of the brain, each embodied on each of the unit slices 19*q* of the slice stack 19*p*, are different from one another.

Figure 5:
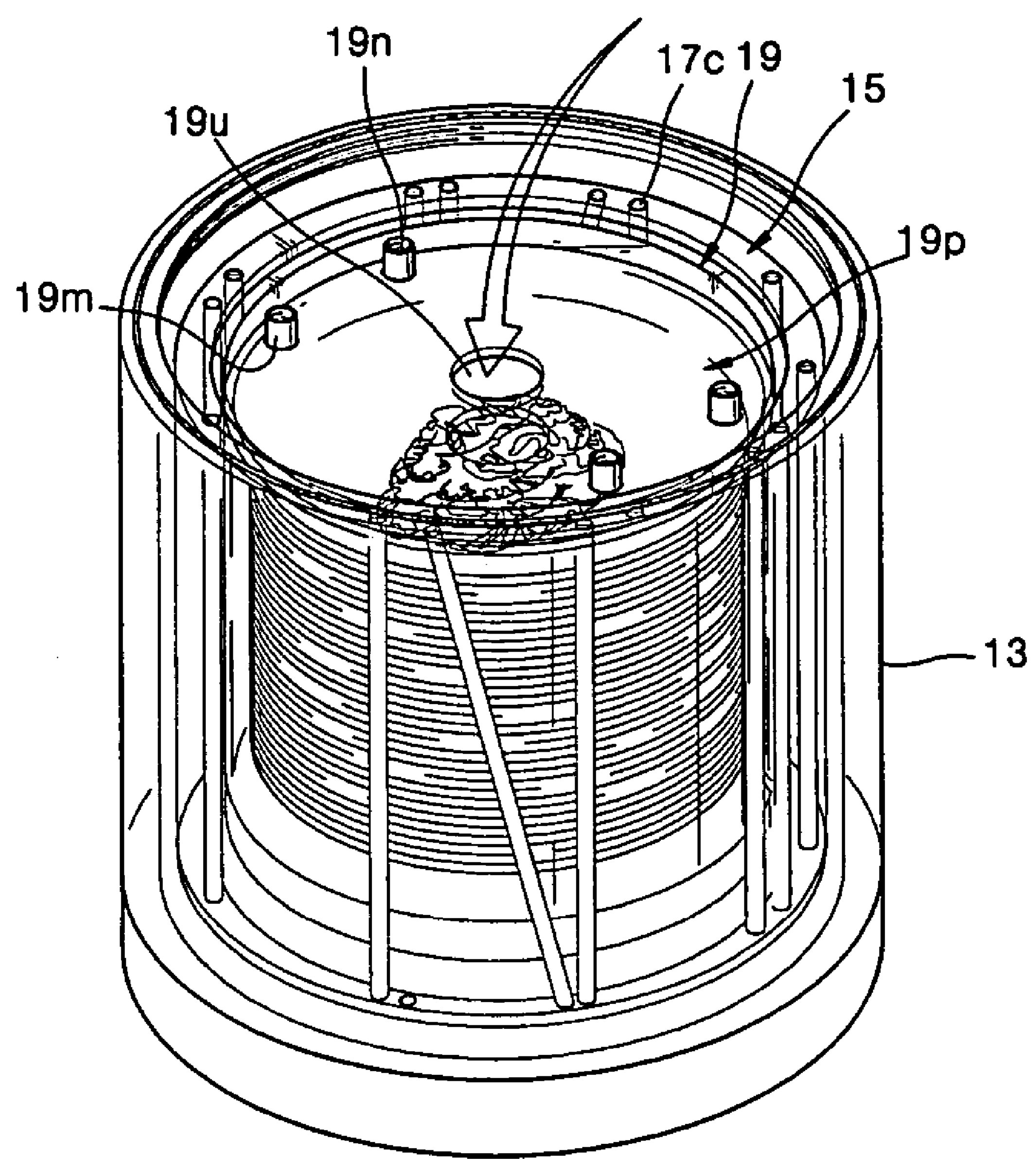
FIG. 5 is a perspective view of the phantom of FIG. 1, from which a lid and a sealing cover are removed.

FIG. 5 is a perspective view of the phantom 11 of FIG. 1, from which the lid 21 and the sealing cover 19*b* are removed. Referring to FIG. 5, the localizer 15 is disposed in the container 13, and the phantom main body 19 is disposed in the localizer 15. The vertical supporting rods 19*m* are fitted into the slice stack 19*p* of the phantom main body 19 such that the slice stack 19*p* is supported by the vertical supporting rods 19*m*.

The upper ends of the vertical supporting rods 19*m* protrude over the slice stack 19*p*. The empty space of the slice stack 19*p* is filled with water by supplying water into the slice stack 19*p* through the through hole 19*u* of the uppermost unit slice 19*q*. Thereafter, the phantom 11 is hermetically sealed, and tomograms of different sections of the phantom 11 are taken using a desired imaging apparatus.

Figure 6:
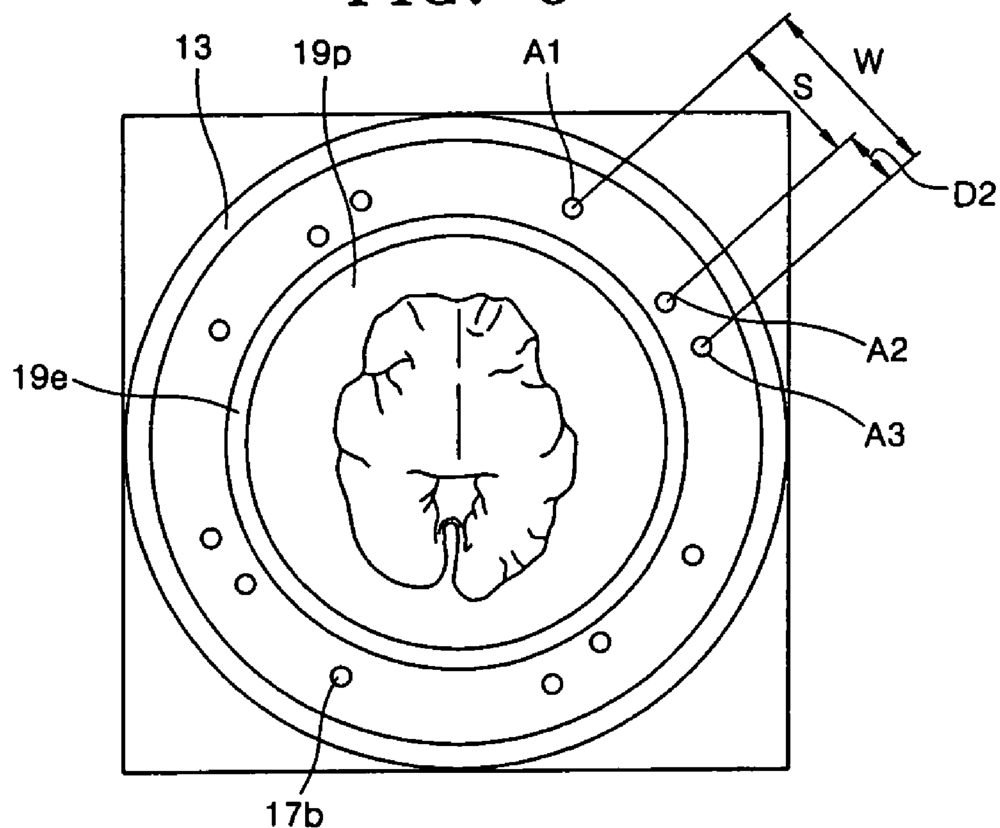
FIG. 6 illustrates a tomogram of a predetermined position of the phantom of FIG. 1 taken by a computed tomography (CT) apparatus.

FIG. 6 illustrates a tomogram of a predetermined position of the phantom 11 of FIG. 1, taken by a computed tomography (CT) apparatus. The inserting rod 17*b* in the acrylic tube 17*a* of the phantom 11 is an acrylic rod.

Referring to FIG. 6, ring-shaped images representing the cross sections of the container 13 and the sidewall 19*e* of the cylindrical case 19*a* of the phantom main body 19 are shown on the tomogram of the phantom 11, and a cross-sectional image of a predetermined position of the brain is shown in the ring-shaped image representing the sidewall 19*e*.

Points A1, A2, and A3 between the two ring-shaped images of the container 13 and the sidewall 19*e* represent the three inserting rods 17*b* of each of the N-shaped indicators 16. Locations of the points A1 and A3 on the tomogram at a predetermined position of the phantom 11 in the axial direction of the phantom 11 are fixed regardless of the height of the unit slice 19*q* of the phantom 11, and thus, the points A1 and A3 serve as fixed reference points. The points A1 and A3 are located a predetermined distance W apart from each other. The point A2, unlike the points A1 and A3, is an indicating point whose location is variable between the fixed points A1 and A3 according to the height in the axial direction of the phantom 11 to which the tomogram corresponds.

Therefore, the height of the interesting position in the phantom 11 from the bottom surface of the case 13 in the axial direction can be obtained by calculating a distance S between the points A1 and A2.

Figure 7:
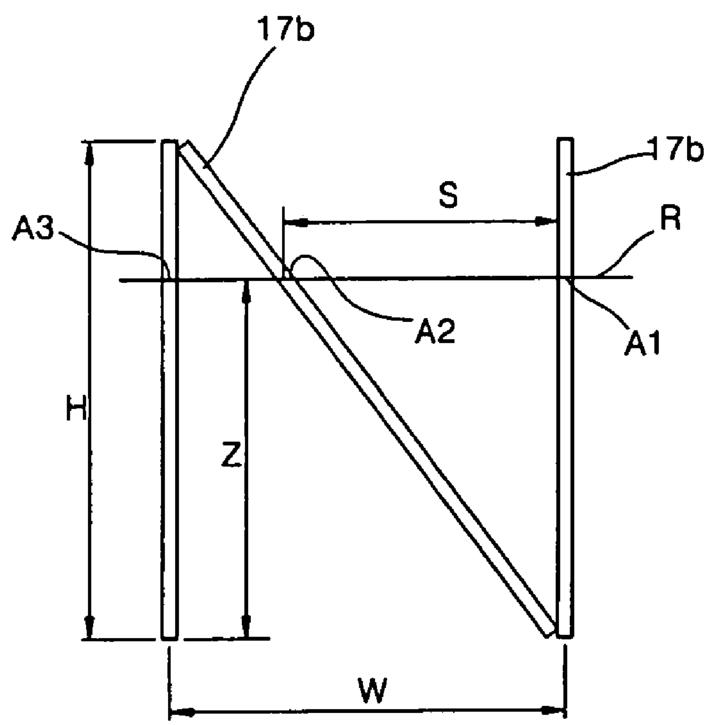
FIG. 7 is a diagram illustrating functions of the localizer of FIG. 1.

In other words, as shown in FIG. 7, the height Z in the axial direction of the phantom 11 to which the tomogram (R) corresponds can be expressed by the following equation:

Z=(H*S)/W where H represents the height of the vertical inserting rod 17*b* and S represents a distance between the points A1 and A2.

Thus the height at the position of interest in the phantom 11 displayed on a computer monitor can be determined by knowing the distances between the fixed points A1 and A3 and the moving point A2 on each tomogram.

Figure 8:
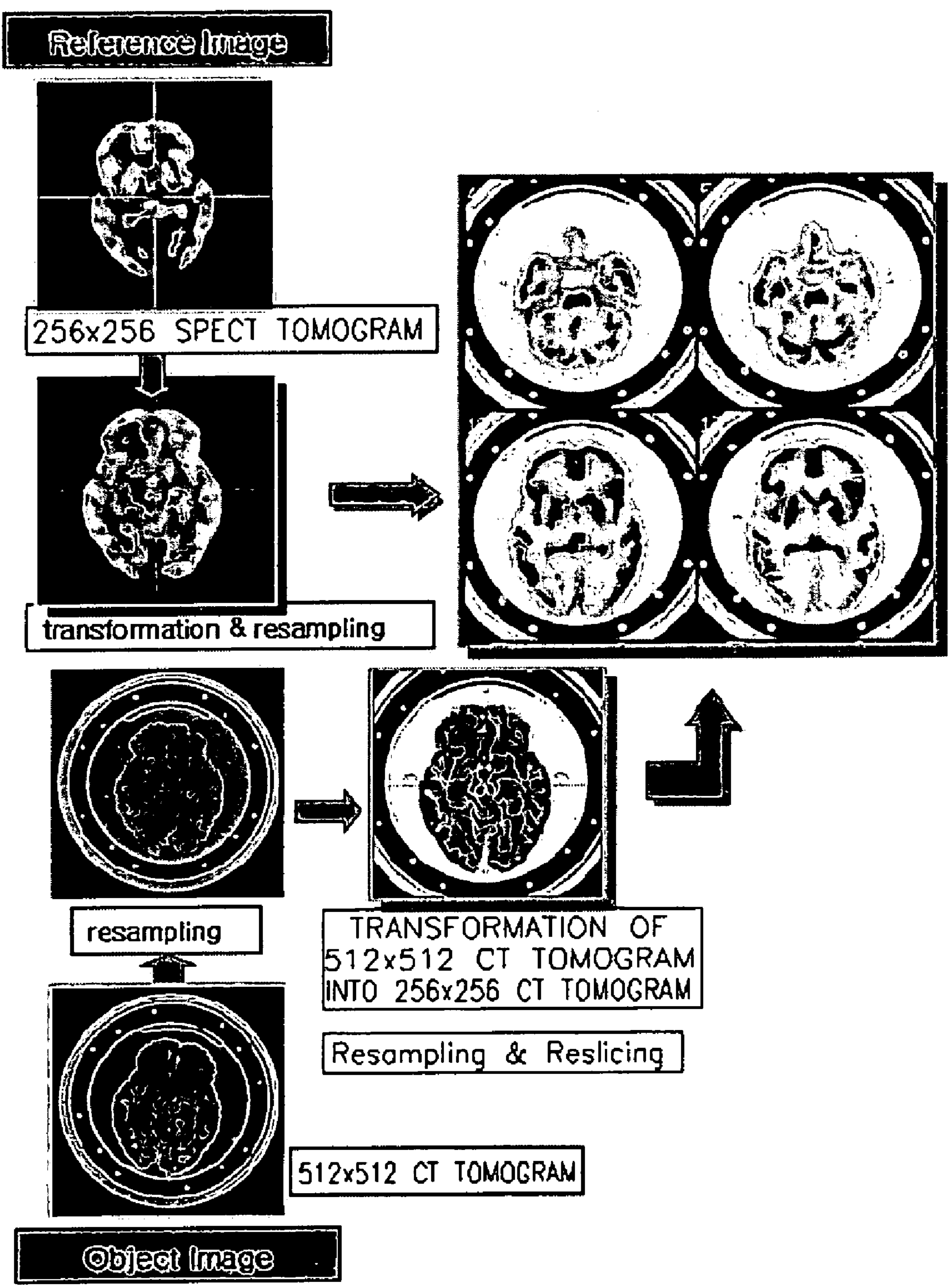
FIG. 8 illustrates tomograms of the phantom of FIG. 1 taken by a CT apparatus and a single photon emission computed tomography (SEPCT) apparatus, and a result of matching the images with each other.

FIG. 8 illustrates tomograms of the phantom of FIG. 1 taken by a CT apparatus and a single photon emission computed tomography (SPECT) apparatus, and a result of matching the tomograms with each other using an image registration technique. Referring to FIG. 8, the tomogram taken by the SPECT apparatus is converted into a 256*256 pixel size image, and the tomogram taken by the CT apparatus, which is originally a 512*512 pixel size image, is also converted into a 256*256 pixel size image. Thereafter, the two converted images are superposed to carry out an image registration.

The two tomograms subjected to the image registration should represent the same position at the same height in the axial direction of the phantom 11. So after getting a CT image that represents the position of the same height in the axial direction as a SPECT image, based on calculating distances between fixed points and an indicating point, the image registration can be carried out.

The image registration is carried out using image registration software in order to test the accuracy of the image registration software.

The tomograms taken by the CT and SPECT apparatuses are superposed, and the accuracy of the image registration software is evaluated based on the degree to which the fixed points on one of the tomograms match with their respective counterparts on the other tomogram. For example, if the fixed points on one of the tomograms exactly match with their respective counterparts on the other tomogram, the image registration software is determined to operate normally. Otherwise, it is determined that the image registration software needs to be corrected.

Figure 9:
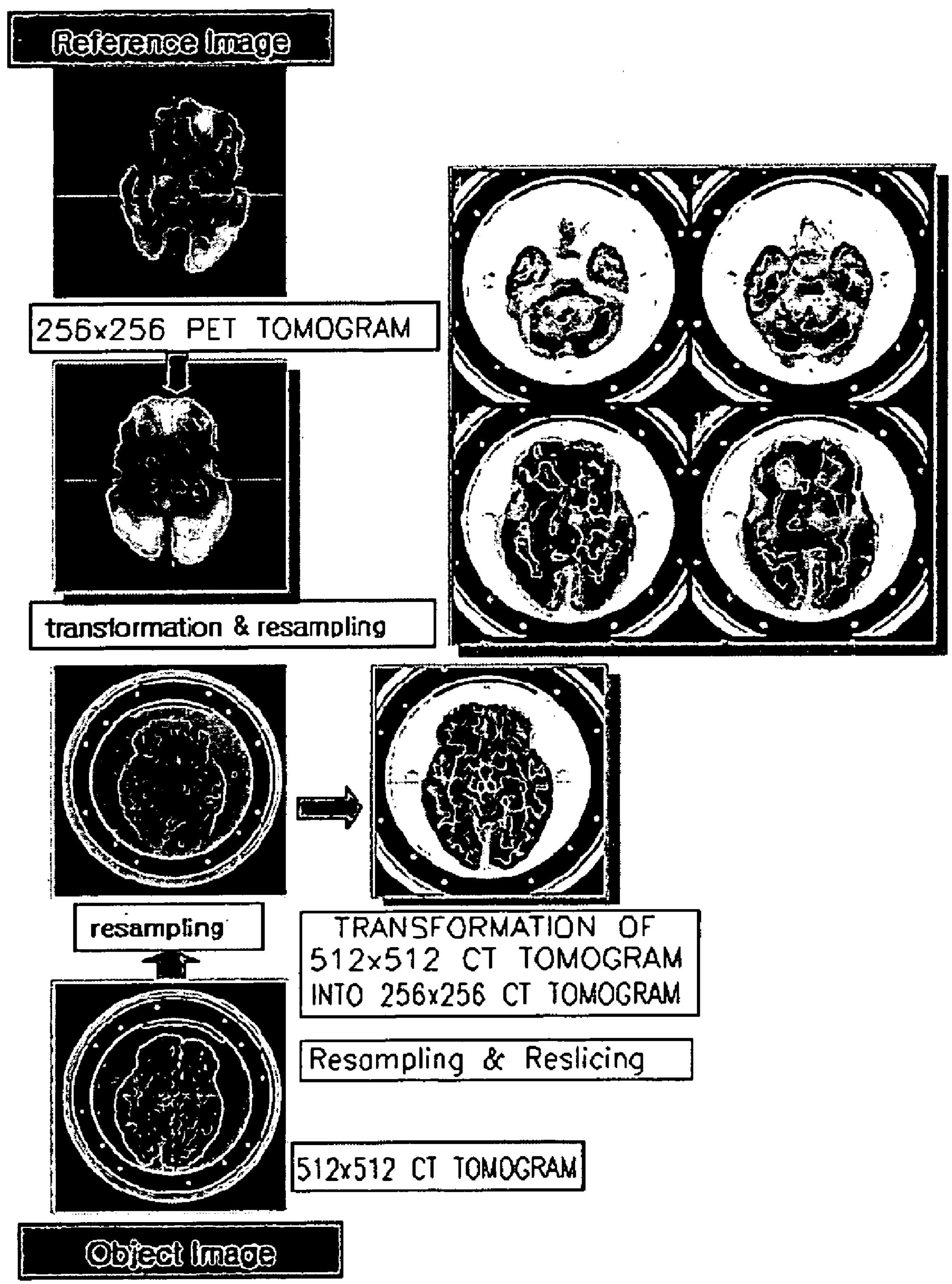
FIG. 9 illustrates tomograms of the phantom of FIG. 1 taken by a CT apparatus and a positron emission tomography (PET) apparatus, and a result of matching the images with each other.

FIG. 9 is a tomogram of the phantom of FIG. 1 taken by a CT apparatus and a PET apparatus, and a result of matching the tomograms with each other based on the image registration. Referring to FIG. 9, the tomograms taken by the CT and PET apparatuses are converted into 256*256 pixel size images. Thereafter, the converted images are resliced in order to get tomograms, which are used for image registration, represent the same height in the axial direction.

Thereafter, superpose one tomogram upon the other tomogram using the image registration software, and then the accuracy of the image registration software is evaluated based on the degree to which the fixed points on one of the tomograms match with their respective counterparts on the other tomogram.

Figure 10:
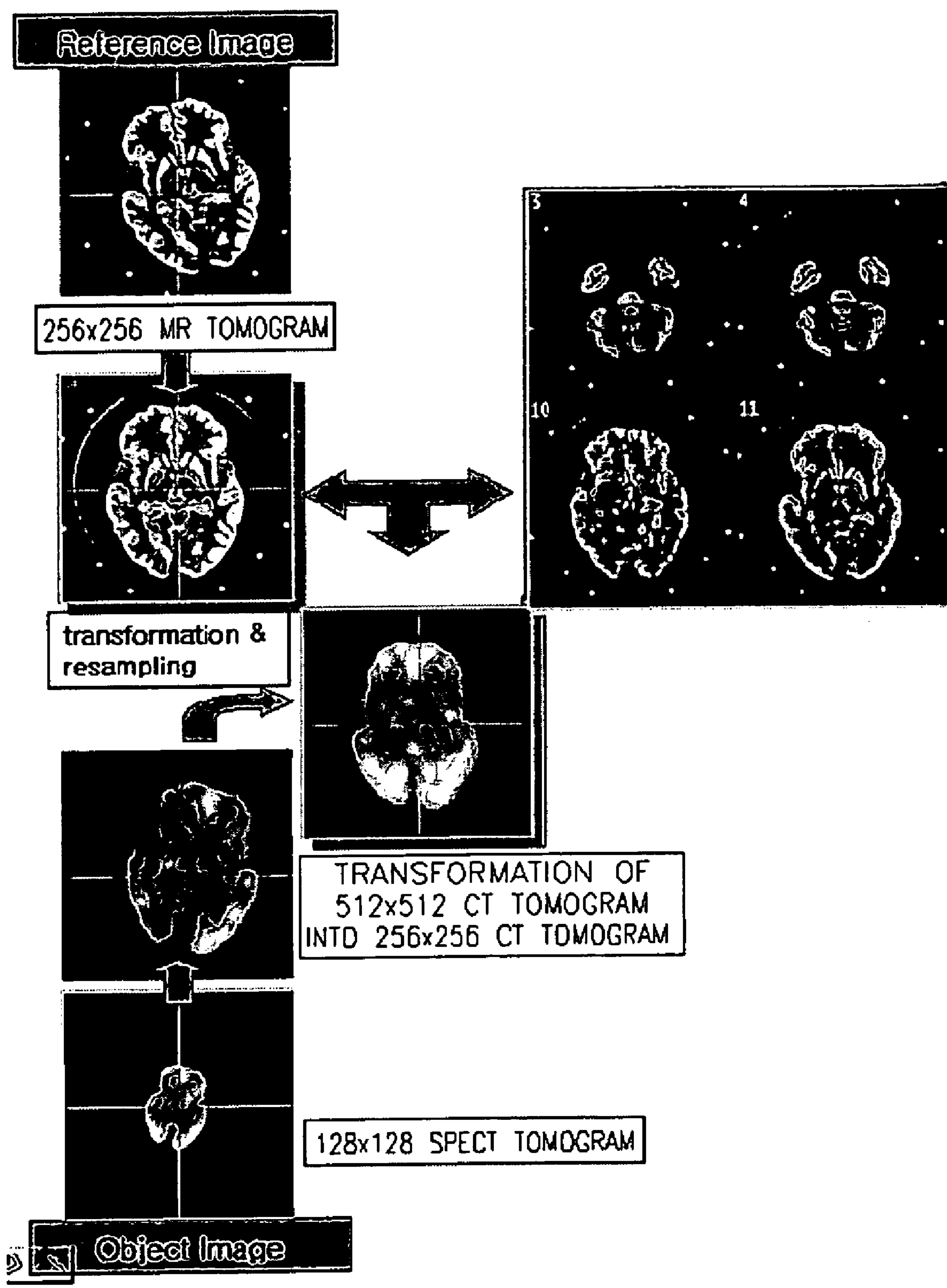
FIG. 10 illustrates tomograms of the phantom of FIG. 1 taken by a magnetic resonance imaging (MRI) apparatus and a SPECT apparatus, and a result of matching the horizontal tomograms with each other.
Figure 11:
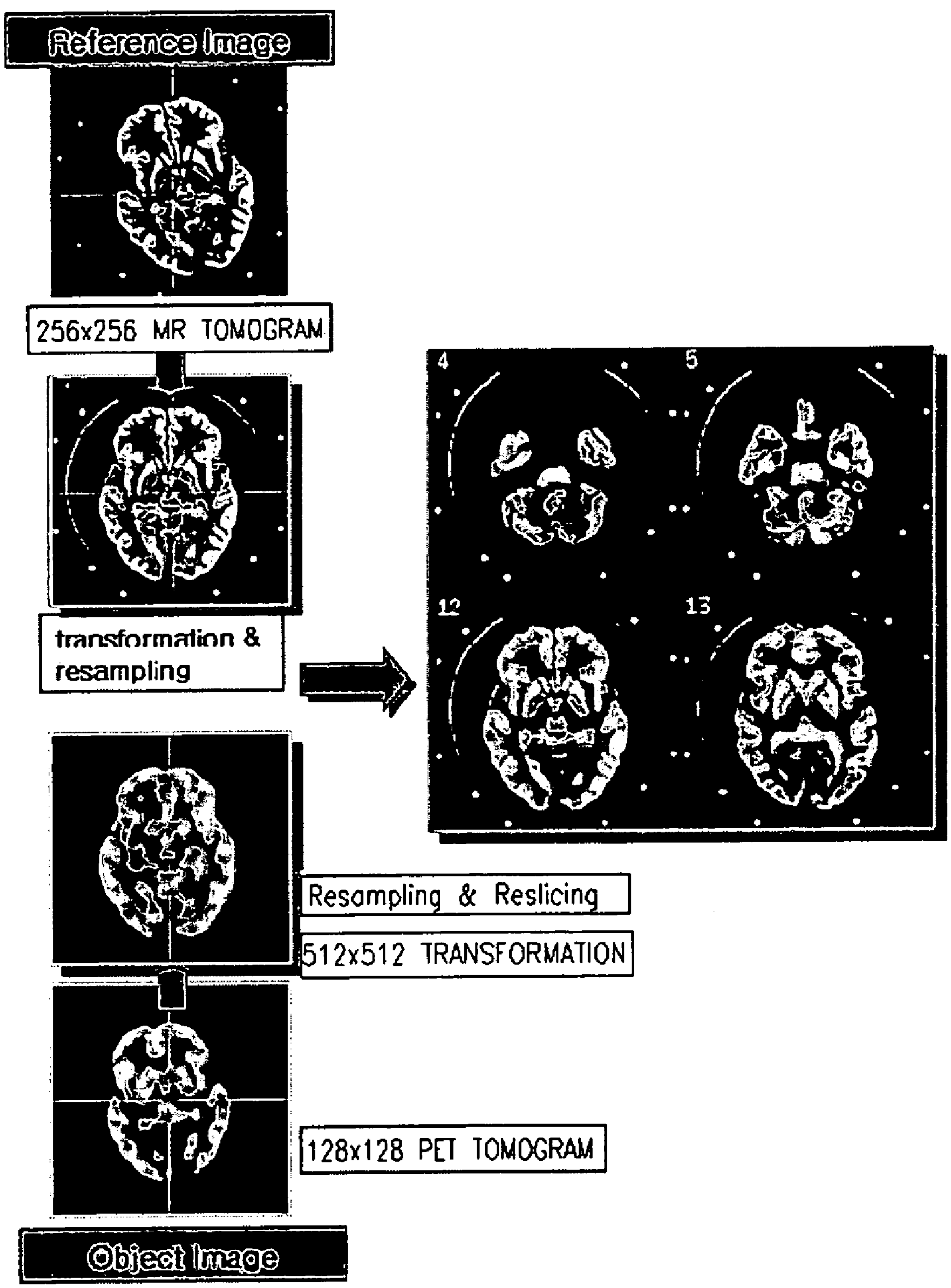
FIG. 11 illustrates tomograms of the phantom of FIG. 1 taken by an MRI apparatus and a PET apparatus, and a result of matching the horizontal tomograms with each another.

FIG. 10 is a tomogram of the phantom of FIG. 1, taken by a MRI apparatus and a SPECT apparatus, and a result of matching the tomograms with each other based on the image registration, and FIG. 11 presents tomograms of the phantom of FIG. 1 taken by MRI and PET apparatuses, and a result of matching the tomograms with each another based on the image registration. Referring to FIGS. 10 and 11, the accuracy of image registration software is evaluated by matching the tomograms taken by the MRI and SPECT apparatuses with each other or the tomograms taken by the MRI and PET apparatuses with each other with the use of the image registration software. The basic principles and method of evaluating the accuracy of the image registration software have already been described above with reference to FIGS. 8 and 9.

Figure 12:
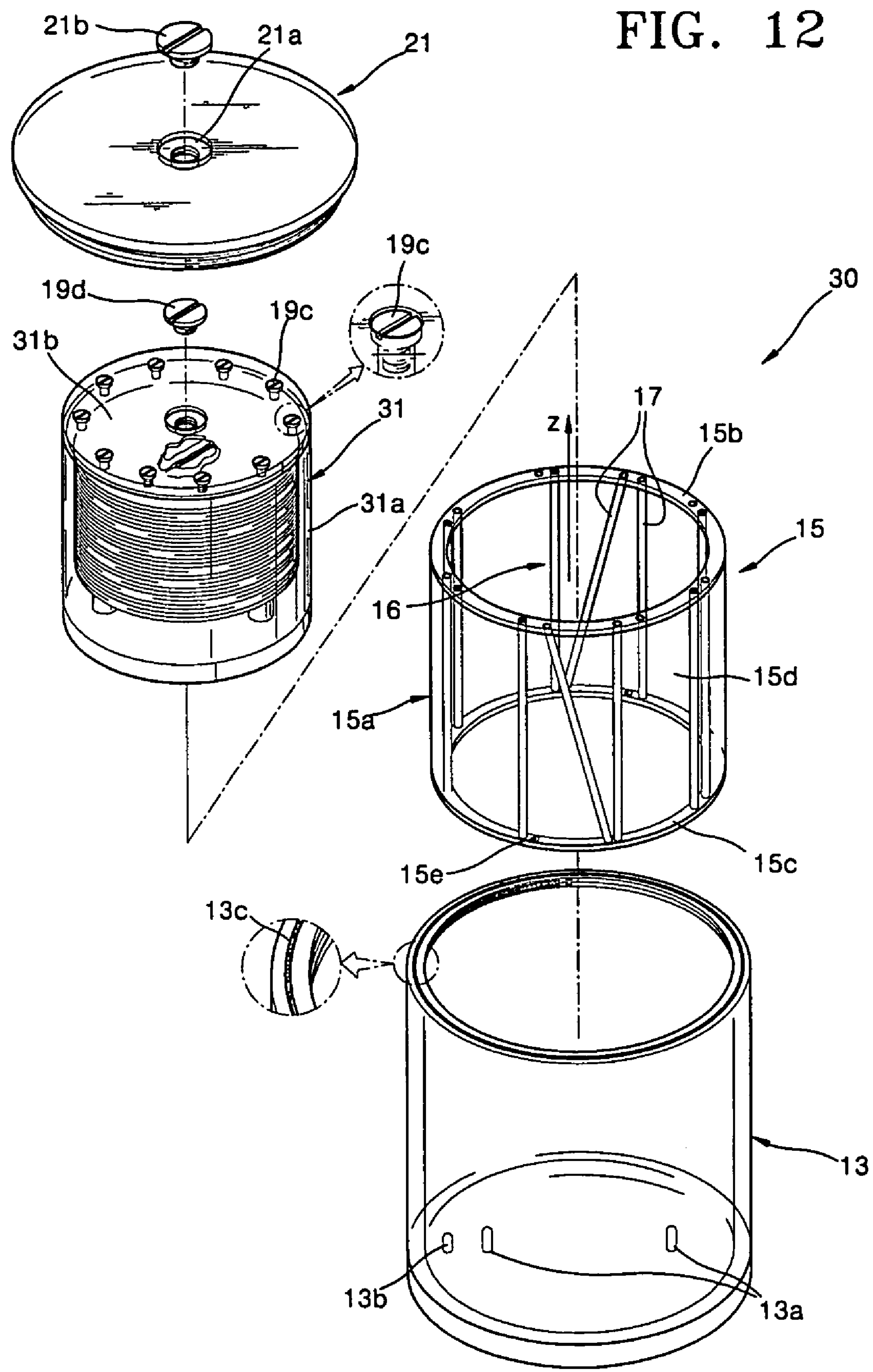
FIG. 12 is an exploded perspective view of a phantom for evaluating the accuracy of image registration software according to a second embodiment of the present invention.

FIG. 12 is an exploded perspective view of a phantom 30 for evaluating the accuracy of image registration software, according to a second embodiment of the present invention. Hereinafter, the same reference numerals represent the same elements, and thus their descriptions will be omitted here. Referring to FIG. 12, the phantom 30 is the same as the phantom 11 of FIG. 1 except for a phantom main body 31.

Figure 13:
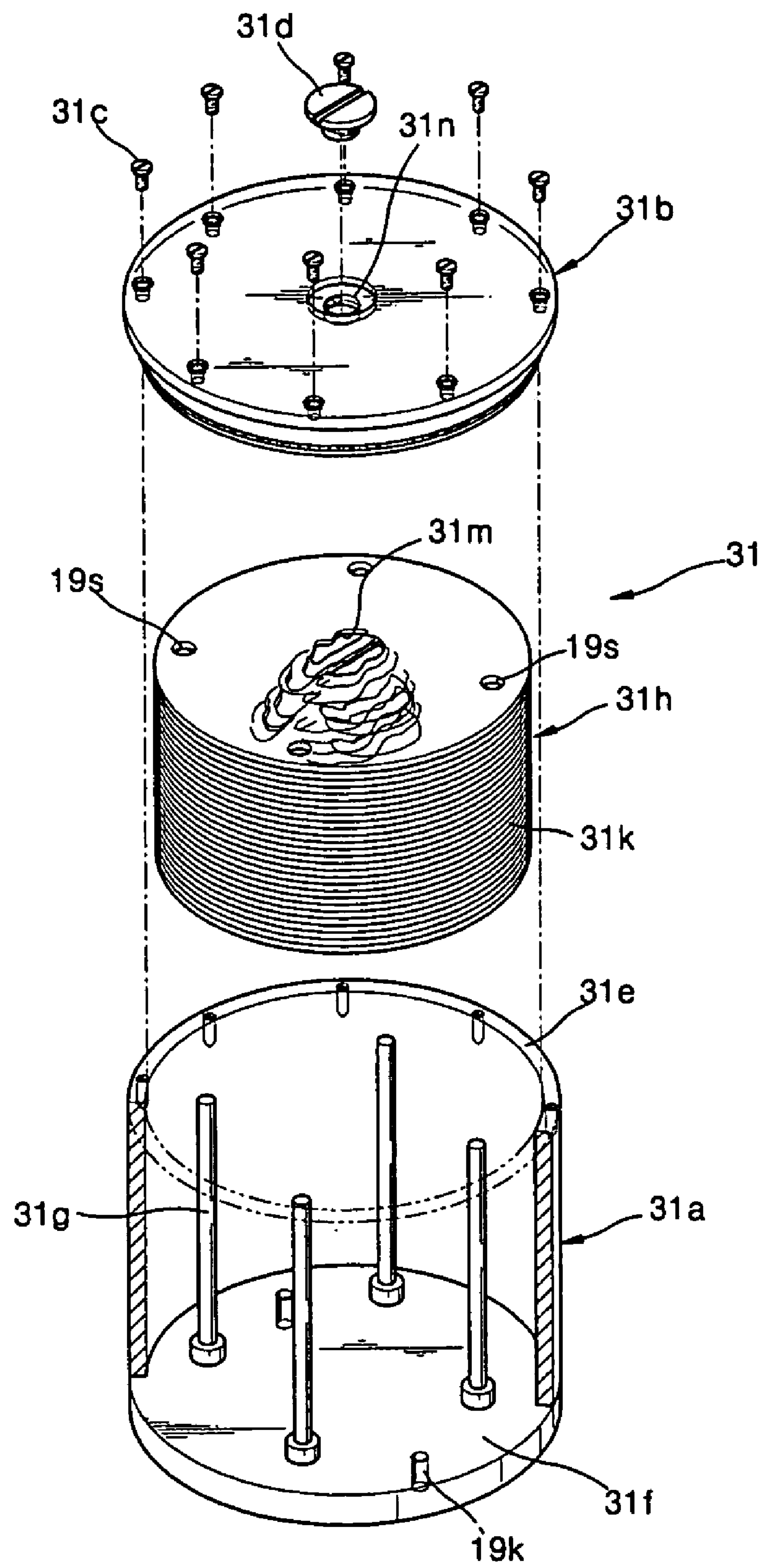
FIG. 13 is a cutaway view of a main body of the phantom of FIG. 12.

FIG. 13 is a cutaway view of the phantom main body 31 of FIG. 12. Referring to FIG. 13, the phantom main body 31 includes a case 31*a*, which includes an empty space therein and can contain water supplied from the outside, a slice stack 31*h*, which is disposed in the case 31*a*, and a sealing cover 31*b*, which covers and hermetically seals the case 31*a*.

The case 31*a* comprises a disc type bottom plate 31*f* with a predetermined thickness and a sidewall 31*e* fixed to the bottom plate 31*f*. A plurality of female screw holes are formed in the top portion of the sidewall 31*e* such that fixing bolts 31*c* can be screwed thereinto. Four vertical supporting rods 31*g* are fixed on the top surface of the bottom plate 31*f*. The vertical supporting rods 31*g* have the same measurements and serve the same functions as the vertical supporting rods 19*m* of FIG. 3.

The slice stack 31*h* comprises a stack of a plurality of unit slices 31*k* stacked sequentially. The slice stack 31*h* has an empty space, which embodies a shape of the entire brain, inside. In order to take an image of the brain embodied in the slice stack 31*h*, the empty space in the slice stack 31*h* must be filled with water, similar to the slice stack 19*p* of FIG. 3. In order to form the empty space inside the slice stack 31*h*, a brain section hole 31*m* is formed in each of the unit slices 31*k* that embody the entire brain when stacked, similar to the slice stack 19*p* of FIG. 3.

An opening hole 31*n* is formed in the center of the sealing cover 31*b*. Water is supplied into the slice stack 31*h* through the opening hole 31*n*, and the opening hole 31*n* can be sealed by an opening/shutting screw 31*d*. A plurality of holes are formed along the circumference of the sealing cover 31*b* so that the fixing bolts 31*c* can be fixed into the sidewall 31*e* through the sealing cover 31*b*.

Figure 14:
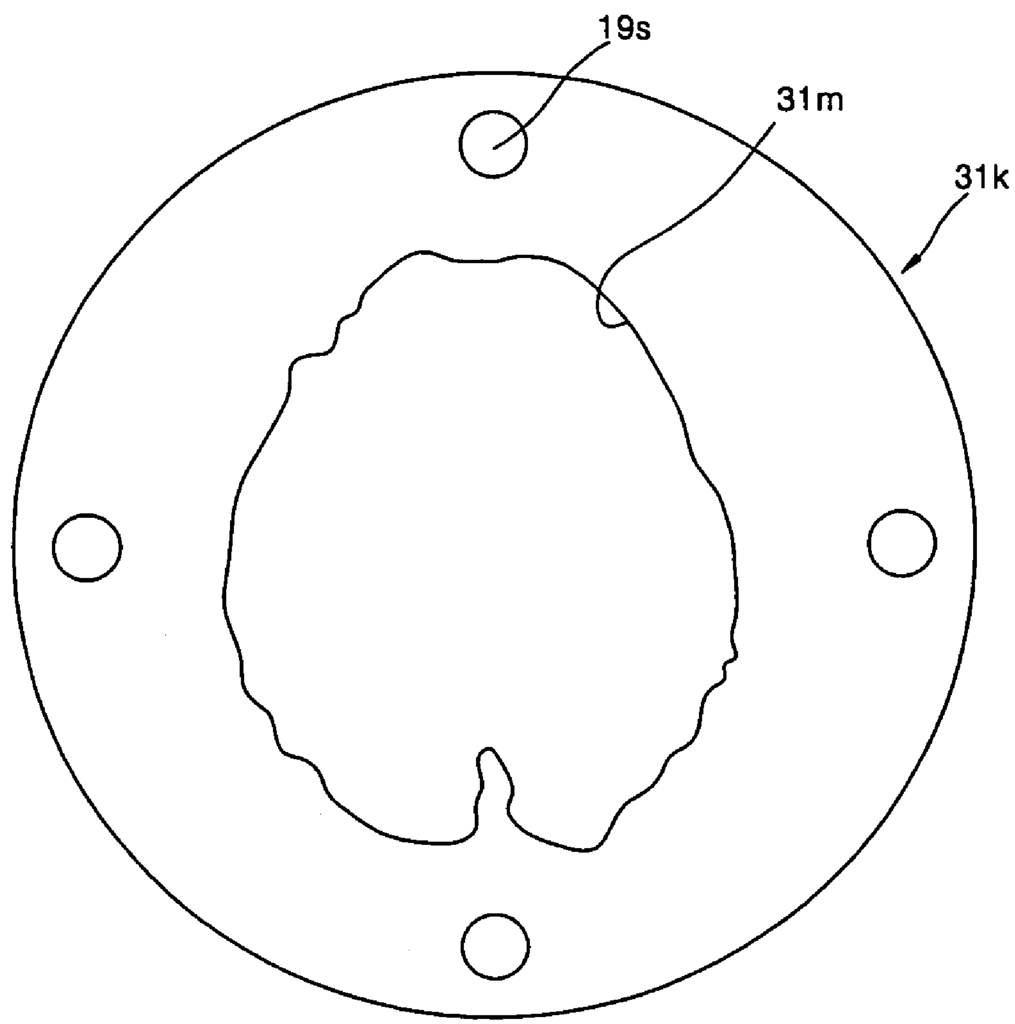
FIG. 14 is a plan view of one of a plurality of unit slices of the main body of FIG. 13.

FIG. 14 is a plan view of one of the plurality of unit slices 31*k* of the slice stack 31*h* of FIG. 13. Referring to FIG. 14, a unit slice 31*k* assumes a simpler shape than the unit slice 19*q* of FIG. 4. While the brain section holes 19*r* on the unit slice 19*q* of FIG. 4 represent the white and gray matter of the brain at a 1:1 ratio, the brain section hole 31*m* on the unit slice 31*k* represents outlines of a predetermined portion of the brain. Each of the unit slices 31*k* represents a horizontal cross section of the brain. The unit slices 31*k* have different shapes of brain section holes 31*m*.

Figure 15:
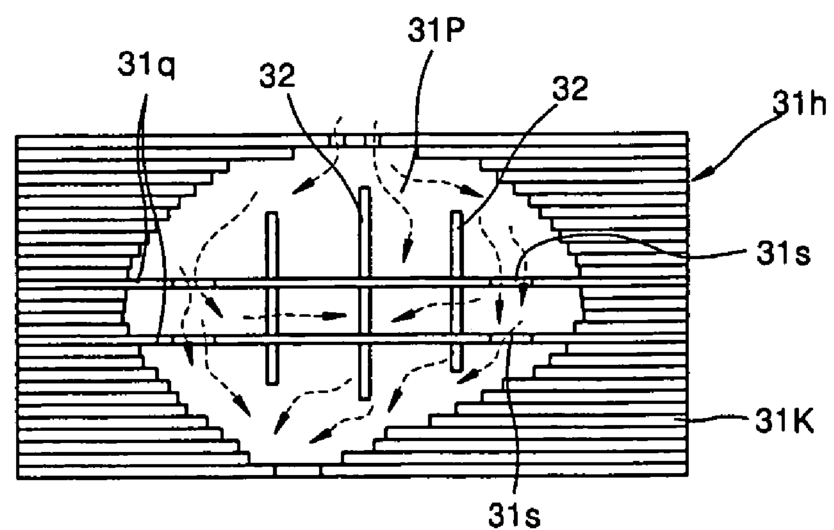
FIG. 15 is a cross-sectional view of a slice stack of FIG. 13.

A plurality of vertical indicating bars 32 of FIG. 15 are disposed in the empty space inside the slice stack 31*h*.

FIG. 15 is a cross-sectional view of the slice stack 31*h* of FIG. 13. Referring to FIG. 15, the slice stack 31*h* includes the plurality of unit slices 31*k* that are stacked on one another, and an inner space 31*p*, which embodies a shape of the brain, is formed inside the slice stack 31*h*. The inner space 31*p* is defined by the brain section hole 31*m* in each of the unit slices 31*k*.

A total of 8 vertical indicating bars 32 are vertically fixed in the inner space 31*p*. Functions of the vertical indicating bars 32 will be described later. Two supporting plates 31*q* vertically fix the vertical indicating bars 32 in the inner space 31*p*.

The supporting plates 31*q* having a predetermined thickness are interposed among the unit slices 31*k* in parallel with each other. The supporting plates 31*q* are formed of the same material of the unit slices 31*k*, and through holes 31*s* are formed in each of the supporting plates 31_q_ such that water can pass through the supporting plates 31_q_.

Figure 16:
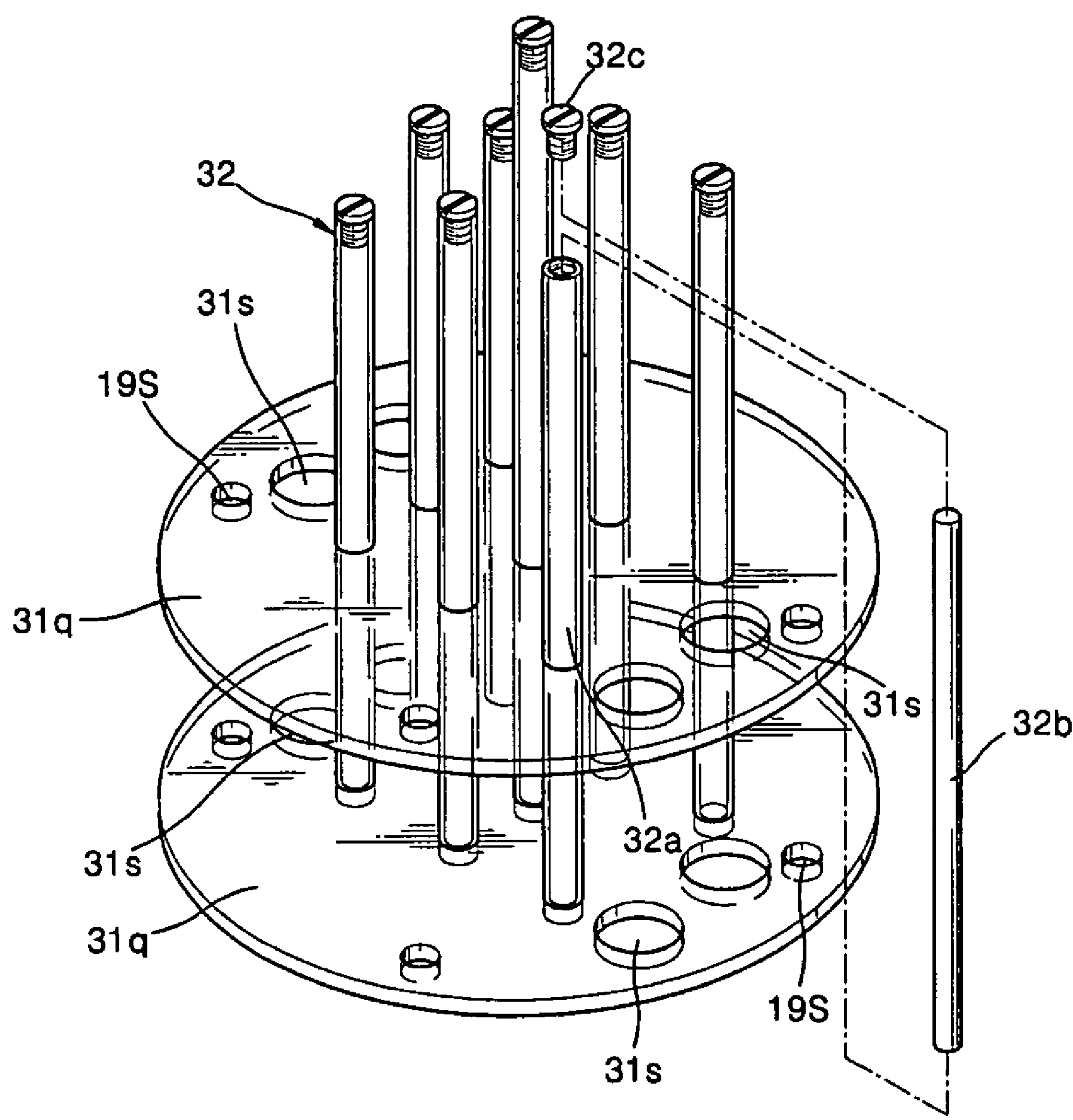
FIG. 16 is an exploded perspective view of vertical indicating bars installed in the slice stack of the phantom of FIG. 12.

FIG. 16 is an exploded perspective view of the supporting plates 31_q_ and the vertical indicating bars 32 coupled thereto. Referring to FIG. 16, the two supporting plates 31_q_ are parallel with each other, and through holes 19_s_ are formed in each of the supporting plates 31_q_ near the boundary of each of the supporting plates 31_q_ such that the vertical supporting rods 31_g_ of FIG. 13 can be inserted therethrough. The through holes 31_s_ are formed in the supporting plates 31_q_ such that water supplied into the slice stack 31_h_ from the outside can pass through the supporting plates 31_q_.

The vertical indicating bars 32 are fixed in the middle of the supporting plates 31_q_. The vertical indicating bars 32, like the N-shaped indicators 16, are provided such that their cross sections can be displayed on an image of the phantom 30. The vertical indicating bars 32 may have different lengths from one another depending on the geometrical shape of the inner space 31_p_ they are disposed.

Each of the vertical indicating bars 32, which are vertically fixed into the supporting plates 31_q_, includes an acrylic tube 32_a_, which has an empty space therein, an inserting rod 32_b_, which is inserted into the acrylic tube 32_a_, and a sealing screw 32_c_, which hermetically seals the acrylic tube 32_a_. The vertical indicating bars 32 comprises the same elements as the N-shaped indicators 16.

When taking an image of the phantom 30 using a CT or MRI apparatus, an acrylic rod is used as the inserting rod 32_b_. And when taking an image of the phantom 30 using a SPECT or PET apparatus, a lead rod is used as the inserting rod 32_b_. Since the acrylic tube 32_a_ can be opened or sealed using the sealing screw 32_c_, the inserting rod 32_b_ inserted in the acrylic tube 32_a_ can be easily replaced by the other one.

Figure 17:
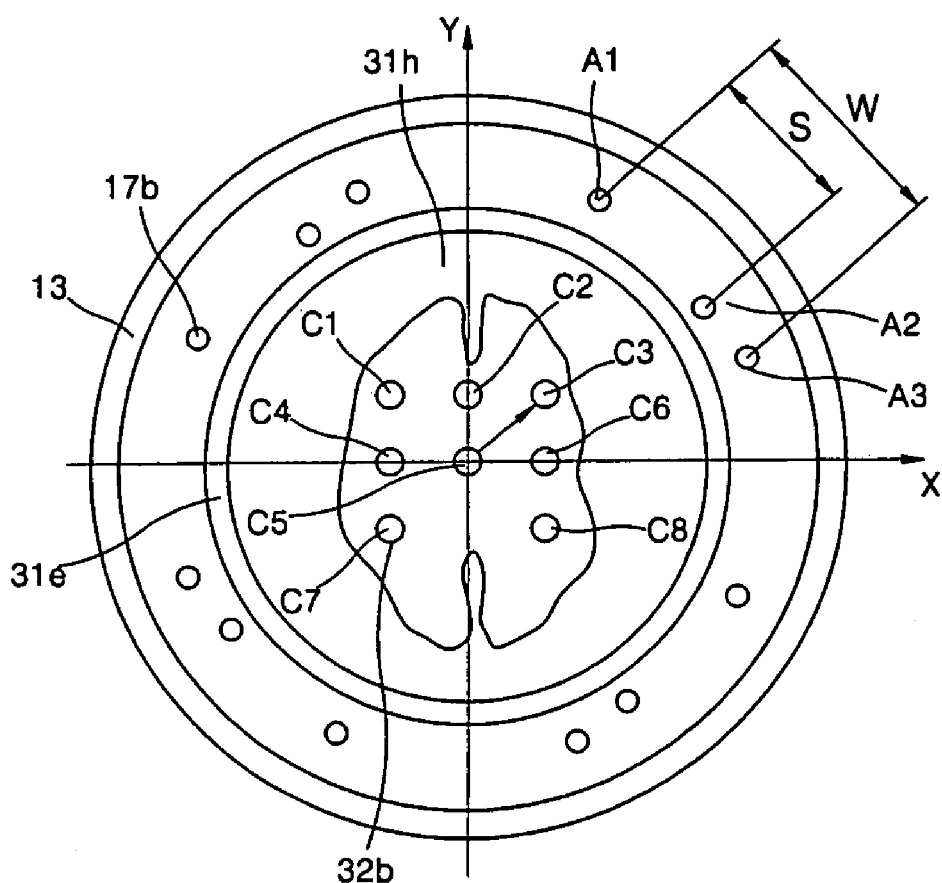
FIG. 17 illustrates a horizontal tomogram of a predetermined position of the phantom of FIG. 12 taken by a CT apparatus.

FIG. 17 illustrates a tomogram of a predetermined position of the phantom 30 of FIG. 12 taken by a CT apparatus. Referring to FIG. 17, cross sections of the container 13 and the sidewall 31_e_ appear on the tomogram of the phantom 30, and a cross-section of the brain, corresponding to the predetermined position of the phantom 30, is shown in the middle of the tomogram. Eight points C1 through C8, which respectively represent eight inserting rods 32_b_, are marked on the tomogram of the position of the brain. The eight fixed points C1 through C8 serve as benchmarks for determining whether the cross section of the predetermined position of the phantom 30 represented by the tomogram is parallel to the bottom surface of the container 13, which will be described later.

Points A1, A2, and A3, which respectively represent cross sections of the three inserting rods 17_b_ of each of the N-shaped indicators 16, are marked on the tomogram between the cross-sectional images of the container 13 and the sidewall 31_e_. The height of the interesting position of the phantom 13 from the bottom surface of the container 13 can be obtained by using distances between the points A1, A2, and A3.

When the fixed points C1 through C8 are mapped on an XY coordinate system such that C4, C5 and C6 are disposed along the X-axis, and C2 and C5 along the Y-axis, and C5 at the origin, the coordinates of the other fixed points, for example C3, are obtained. The distance from the bottom surface of the container 13 to the point C3 can be obtained using the distances between the points A1, A2, and A3.

Figure 18:
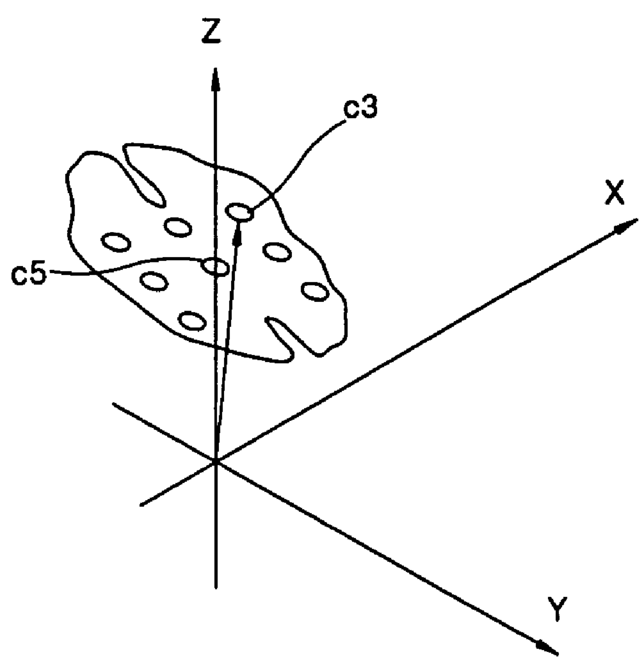
FIG. 18 illustrates functions of the vertical indicating bars.

FIG. 18 illustrates functions of the vertical indicating bars 32. More specifically, FIG. 18 illustrates a result of transferring the tomogram of FIG. 17 on an XYZ coordinate system. Referring to FIG. 18, supposing that an intersection point between the bottom surface of the container 13 and a line perpendicular to the bottom surface of the container 13 passing through C5 is set as the origin of the XYZ coordinate system, coordinates of C3 can be obtained using the above-mentioned method, and a vector representing C3 with respect to the origin can be obtained using the coordinates of C3.

Vectors respectively representing the other fixed points with respect to the origin can also be obtained using their coordinates. Thus, tomograms at a position of interest of the phantom 30, taken by different imaging apparatuses, such as CT and MRI apparatuses or SPECT and PET apparatuses, can be three-dimensionally compared with each other. In other words, if the images at the same position in the axial direction of the phantom, taken using each imaging apparatus, are obtained, the accuracy of the image registration software can be evaluated two-dimensionally by observing the degree to which the fixed points C1 through C8 on one of the tomograms match with their respective counterparts on the other tomogram. In addition, the accuracy of the image registration software can also be evaluated three-dimensionally by calculating vectors of the fixed points on each of the tomograms and comparing them.

If the vectors representing the fixed points on one of the tomograms match with their respective counterparts on the other tomogram, the image registration software is determined to operate normally. Otherwise, it is determined that cross sections of the phantom 30 represented by the tomograms are not parallel with each other, which means the image registration software is not accurate.

Figure 19:
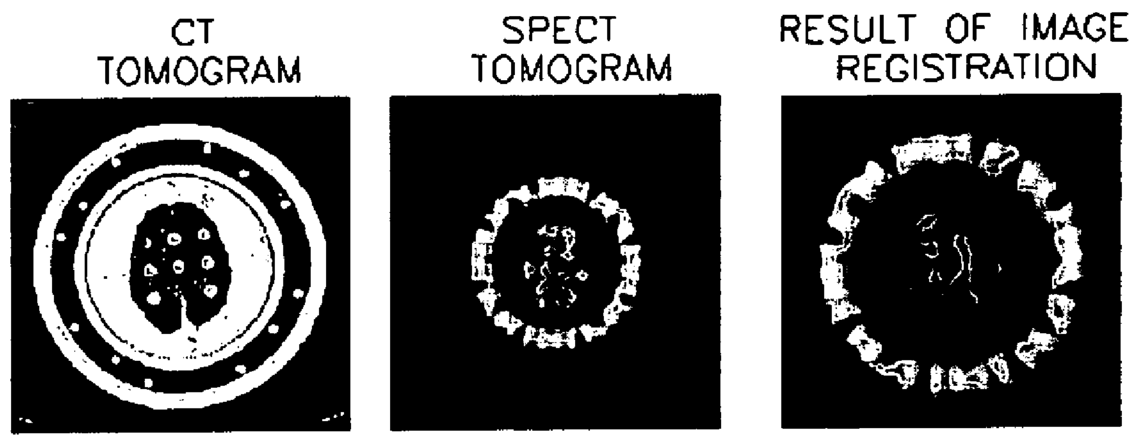
FIG. 19 illustrates tomograms of the phantom of FIG. 12 taken by a CT apparatus and a SPECT apparatus, and a result of matching the horizontal tomograms with each other.
Figure 20:
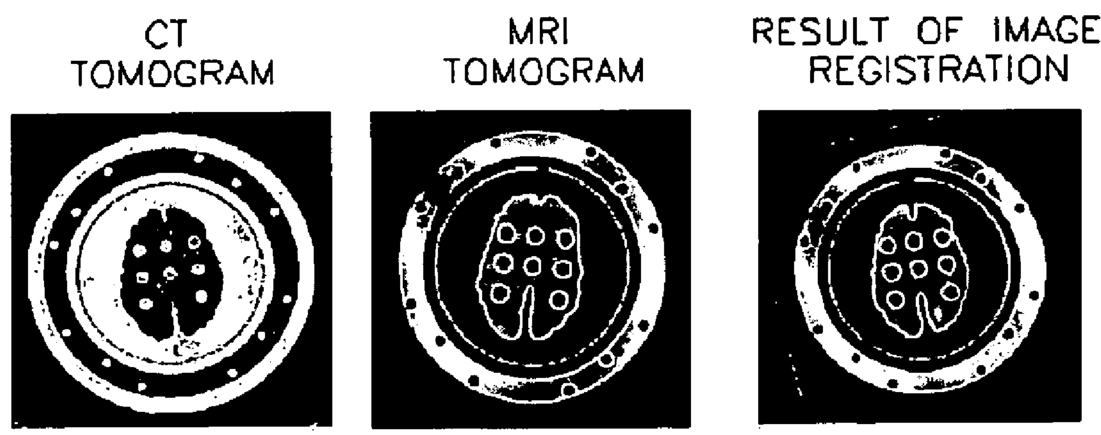
FIG. 20 illustrates tomograms of the phantom of FIG. 12 taken by a CT apparatus and an MRI apparatus, and a result of matching the horizontal tomograms with each other.

FIG. 19 illustrates tomograms of the phantom of FIG. 12 taken by a CT apparatus and a SPECT apparatus, and a result of matching the tomograms with each other using image registration software, and FIG. 20 illustrates tomograms of the phantom of FIG. 12 taken by a CT apparatus and an MRI apparatus, and a result of matching the tomograms with each other using image registration software.

Figure 21:
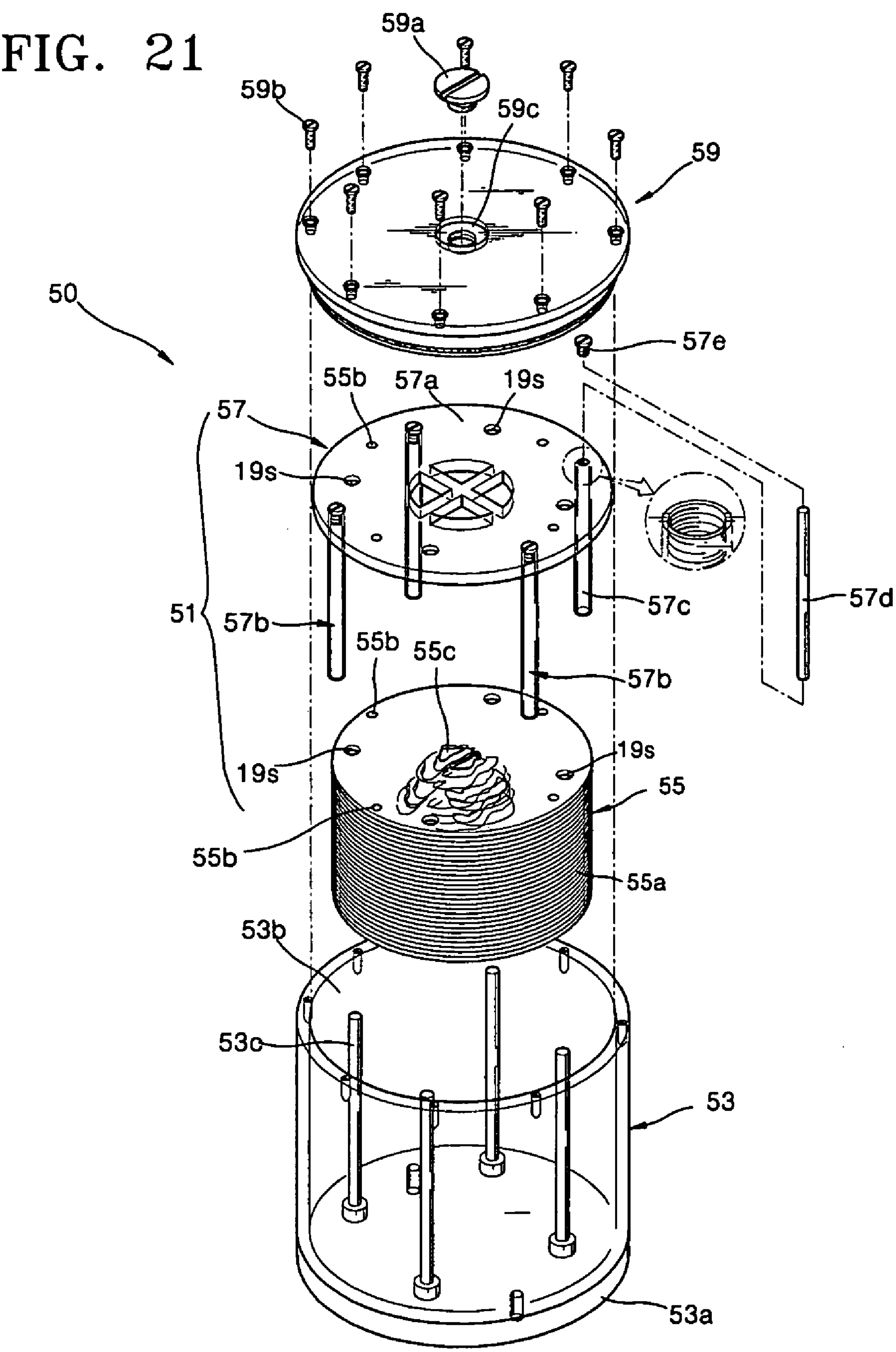
FIG. 21 is an exploded perspective view of a phantom for evaluating the accuracy of image registration software according to a third embodiment of the present invention.

FIG. 21 is an exploded perspective view of a phantom 50 for evaluating the accuracy of image registration software according to a third embodiment of the present invention. Referring to FIG. 21, the phantom 50 includes a container 53, which can contain water therein and includes four vertical supporting rods 53_c_, a phantom main body 51, which is disposed in the container 53, and a lid 59, which hermetically seals the container 53.

The container 53 includes a bottom plate 53_a_, which is disk-shaped, and a sidewall 53_b_, which is cylindrical. The vertical supporting rods 53_c_ are fixed on the bottom plate 53_a_. The vertical supporting rods 53_c_ are acrylic rods that pass through through holes 19_s_ of a slice stack 55 so that they can support the slice stack 55.

The phantom main body 51 comprises the slice stack 55 and an indicator 57.

The slice stack 55 comprises a plurality of unit slices 55_a_. Lung section holes 55_c_, which embody a cross section of the lungs, are formed in the unit slices 55_a_. The slice stack 55 has an empty space embodying the lungs.

Auxiliary holes 55_b_ are further formed in the slice stack 55 near the outer boundary of the slice stack 55 such that they can be filled with water. The auxiliary holes 55_b_ filled with water are represented by points on a tomogram of the phantom 50.

The indicator 57 comprises a supporting slice 57_a_, which covers the top surface of the slice stack 55, and four vertical indicating bars 57_b_, which are fixed to the bottom surface of the supporting slice 57_a_ and extend vertically downward from the bottom surface of the supporting slice 57_a_. The vertical indicating bars 57_b_ have the same functions as the vertical indicating bars 32 in the second embodiment of the present invention.

Each of the vertical indicating bars 57_b_ comprises an acrylic tube 57_c_, an upper end of which can be exposed to the outside over the supporting slice 57_a_, an inserting rod 57_d_, which is disposed in the acrylic tube 57_c_, and a sealing screw 57_e_, which hermetically seals the upper end of the acrylic tube 57_c_. As described above, an acrylic or lead rod can be selectively used as the inserting rod 57_d_. Two of the four vertical indicating bars 32 are shorter than the other two vertical indicating bars 32.

A lid 59 hermetically seals the container 53 with the phantom main body 51 disposed in the container 53. A plurality of holes are formed near the boundary of the lid 59 so that fixing bolts 59_b_ can be fixed into the container 53 passing through the lid 59.

A water supply hole 59_c_ is formed in the middle portion of the lid 59. The water supply hole 59_c_ can be sealed by an opening/shutting screw 59_a_.

Figure 22:
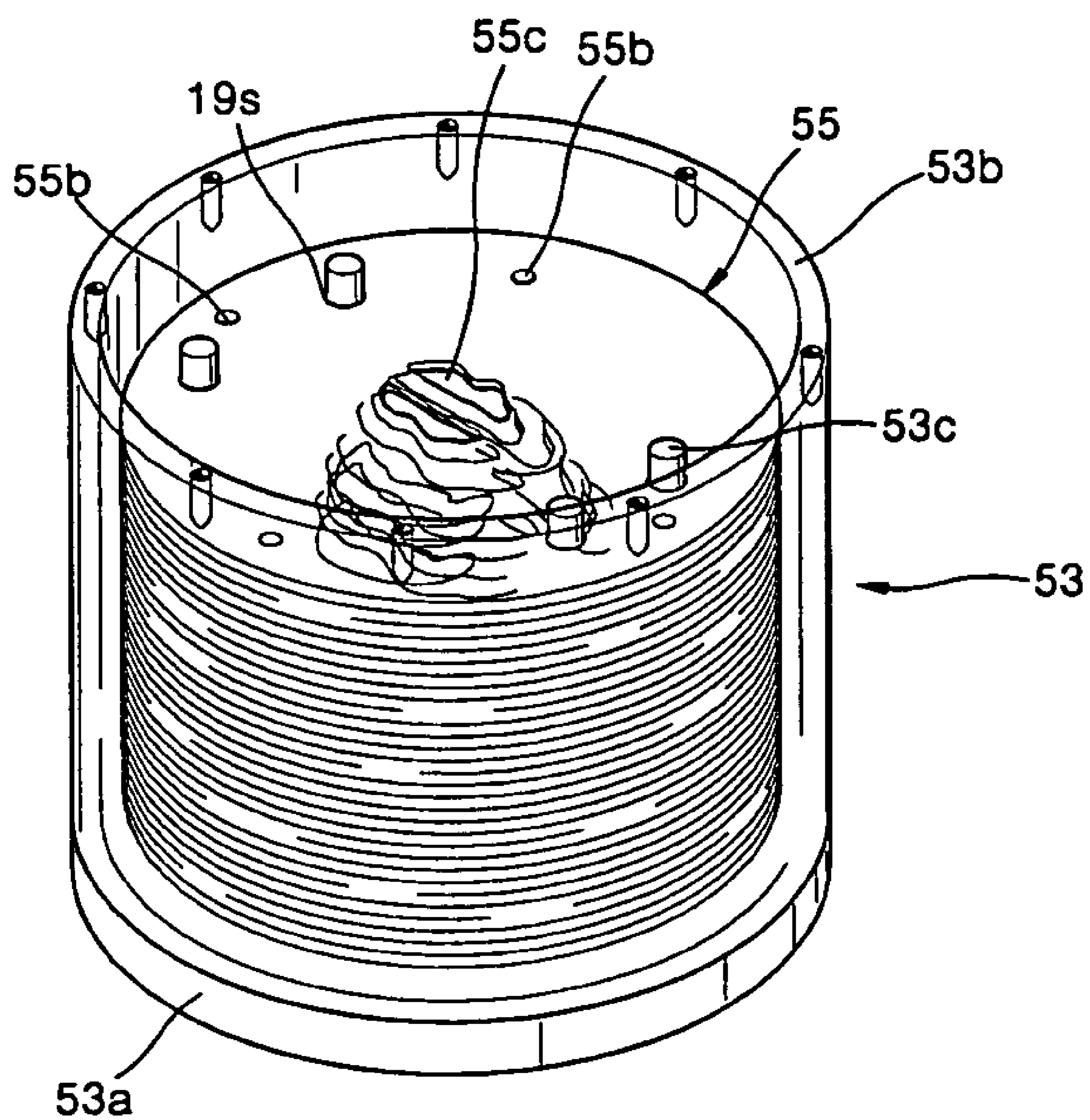
FIG. 22 is a perspective view of the phantom of FIG. 21, from which a lid is removed.

FIG. 22 is a perspective view of the phantom 50 of FIG. 21, from which the lid 59 and the indicator 57 are removed. Referring to FIG. 22, the unit slices 55_a_ can be neatly stacked in the container 53 due to the vertical supporting rods 53_c_. The circumferential boundary of the slice stack 55 does not contact the inner sidewall of the container 53 such that an empty space is formed therebetween. The empty space is filled with water.

Figure 23:
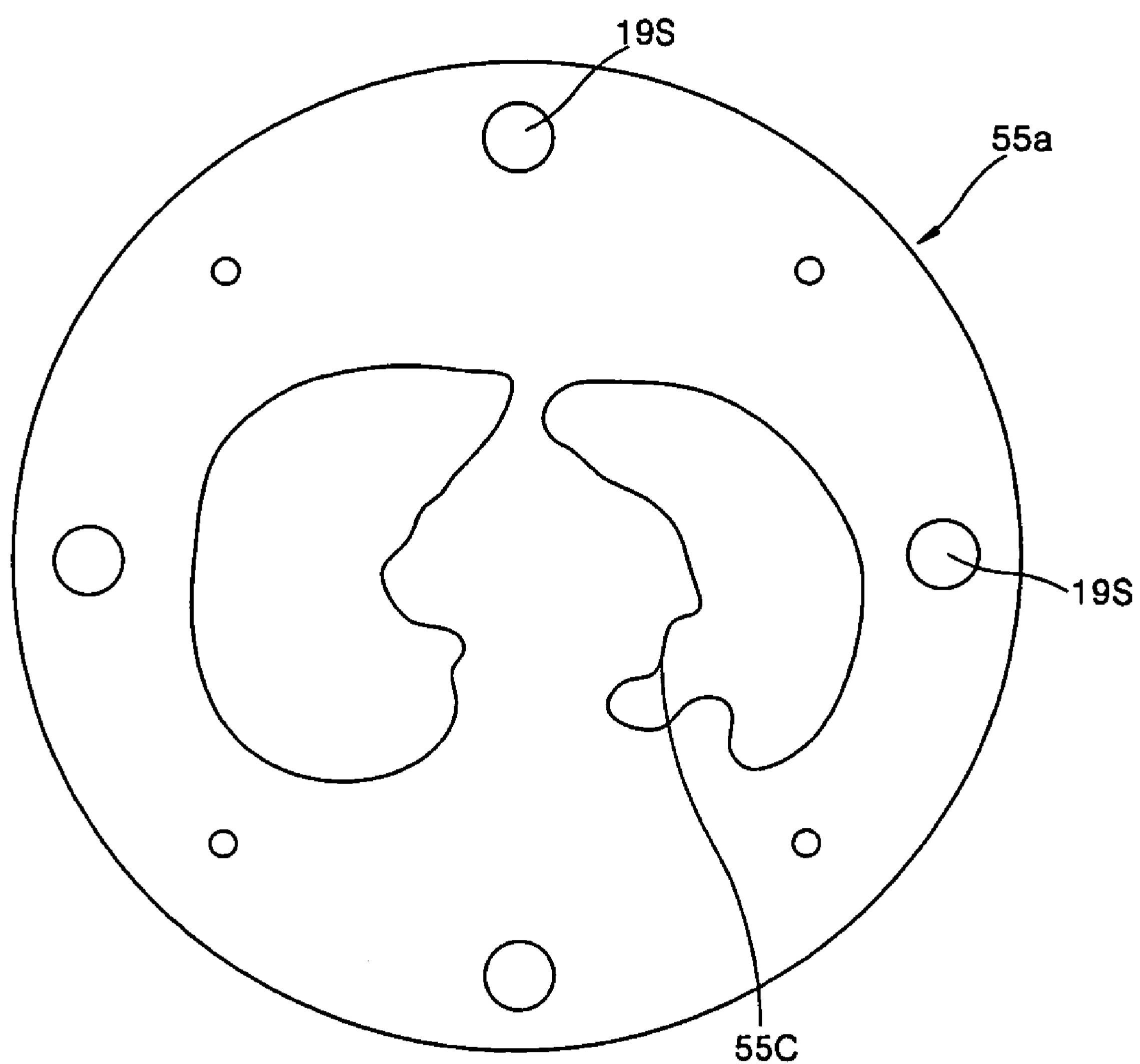
FIG. 23 is a plan view of one of a plurality of unit slices of a slice stack of FIG. 21.

FIG. 23 is a plan view of one of the plurality of unit slices 55_a_ of the slice stack 55 of FIG. 21. Referring to FIG. 23, four through holes 19_s_ and four auxiliary holes 55_b_ are formed in a unit slice 55_a_ near the boundary of the unit slice 55_a_. Lung section holes 55_c_ on the unit slice 55_a_ represent a cross section of a predetermined position in the axial direction of the lungs.

Figure 24:
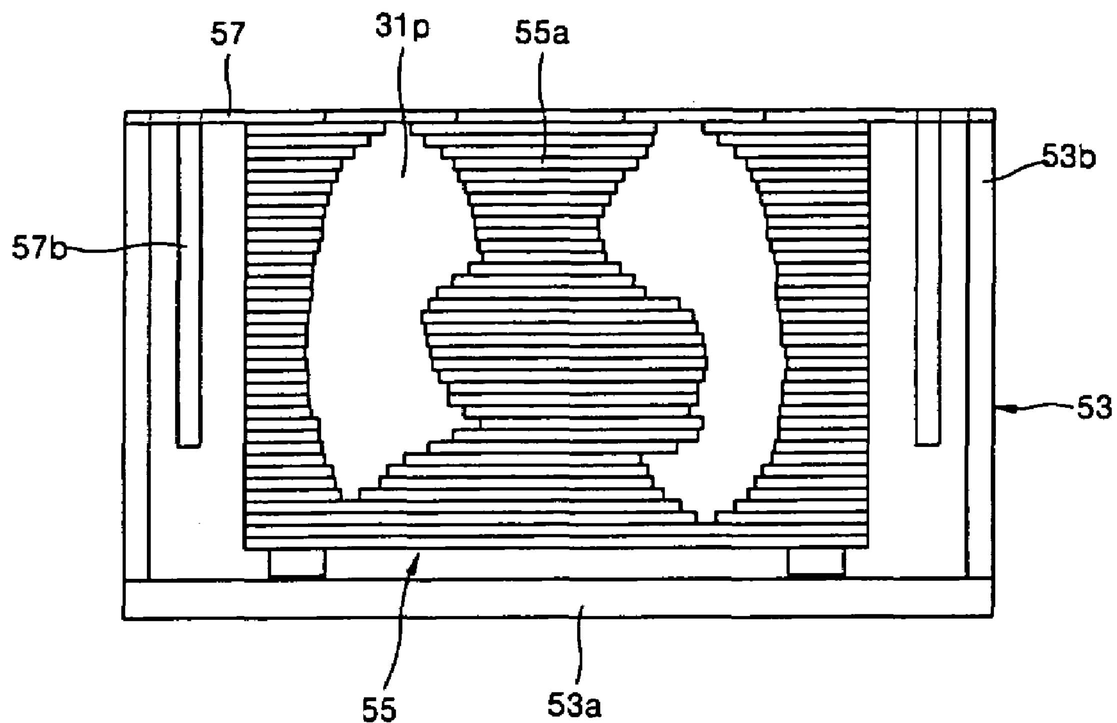
FIG. 24 is a cross-sectional view of the phantom of FIG. 21.

FIG. 24 is a cross-sectional view of the phantom 50 of FIG. 21. Referring to FIG. 24, the plurality of unit slices 55_a_, which are stacked sequentially, has an inner space 31_p_, which embodies a shape of the lungs. The inner space 31_p_ is defined by the lung section holes 55_c_ formed through each of the unit slices 55_a_.

The vertical indicating bars 57_b_ are disposed between the sidewall 53_b_ and the slice stack 55. Before tomographing the phantom 50, the inner space 31_p_ and a space where the vertical indicating bars 57_b_ are filled with water.

Figure 25:
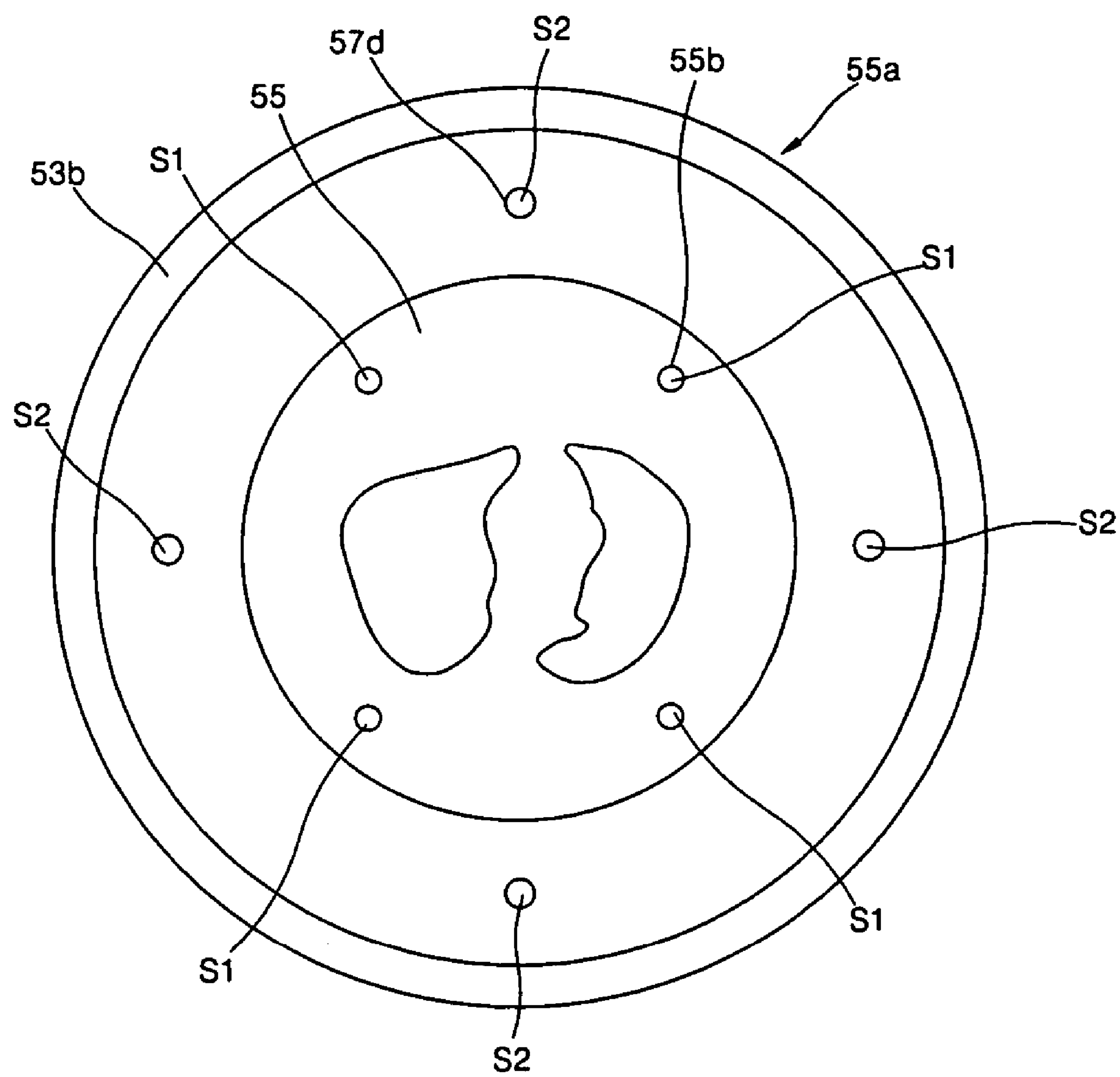
FIG. 25 illustrates a tomogram of a predetermined position of the phantom of FIG. 21 taken by a CT apparatus.

FIG. 25 illustrates a tomogram at a position of interest of the phantom 50 of FIG. 21 taken by a CT apparatus. Referring to FIG. 25, cross sections of the sidewall 53_b_ and the inserting rod 57_b_ of each of the vertical indicating bars 57_b_ are represented by points. Points S1 represent cross sections of pillars of water filling the auxiliary holes 55_b_. Accuracy of image registration software is evaluated by using the points S1 and other points S2. In other words, tomograms of the predetermined position of the phantom 50 taken by different imaging apparatuses are superposed on one another, and then the accuracy of the image registration software is evaluated depending on the degree to which fixed points, such as the points S1 and S2, on one of the tomograms match with their respective counterparts on another tomogram.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A phantom for evaluating the accuracy of image registration software based on a result of matching tornograms of a predetermined position of the phantom taken using two or more imaging apparatuses, the phantom comprising:

a container, which can contain water therein;

a phantom main body, which is installed in the container, the phantom main body having a case with an empty space therein that embodies a predetermined portion of a human body, the empty space of the case adapted to be filled with water, the phantom main body including a slice stack having a plurality of unit slices sequentially stacked in the case and has an empty space that embodies the predetermined portion; and a localizer disposed between the phantom main body and an inner sidewall of the container, the localizer configured to indicate a height in an axial direction of the phantom to which the tornograms correspond.

2. The phantom of claim 1, wherein the unit slices are plates with a predetermined thickness stacked on a bottom surface of the case, each unit slice includes holes therethrough to allow the unit slices to represent cross sections of the predetermined portion of the human body, and the empty space inside the slice stack is defined by the holes in each of the unit slices when the unit slices are stacked.

3. The phantom according to claim 1, further comprising at least one vertical indicating bar, which extends vertically upward from a bottom surface of the container such that its cross section appears on each of the tornograms of the phantom.

4. A phantom for evaluating the accuracy of image registration software based on a result of matching tornograms of a predetermined position of the phantom taken using two or more imaging apparatuses, the phantom comprising:

a container adapted to contain water therein;

a phantom main body installed in the container, the phantom main body having an empty space therein that embodies a portion of the human body, the empty space adapted to container water therein; and a localizer disposed between the phantom main body and an inner sidewall of the container, the localizer configured to indicate a height in an axial direction of the phantom to which the tornograms correspond, wherein the localizer further comprises:

a frame comprising a main body having a cylindrical shape with a predetermined height and contains the phantom main body therein, the frame including upper and lower rings having a predetermined width and are respectively fixed to upper and lower ends of the main body; and at least one N-shaped indicator coupled to the upper and lower rings at both the upper and lower ends of the main body such that its cross section appears on each of the tornograms of the phantom, the at least one N-shaped indicator including a plurality of indicating bars, two of which extend vertically upward from the lower ring and are separated by a predetermined distance, and at least one of which is slanted between the two indicating bars such that its lower end is located in a vicinity of the lower end of one of the two indicating bars disposed vertically and its upper end is located in the vicinity of the lower end of the other indicating bar disposed vertically.

5. The phantom of claim 4, wherein at least two N-shaped indicators are evenly distributed around the circumference of the phantom main body.

6. The phantom of claim 4, wherein each of the indicating bars comprises:

an acrylic tube, which is fixed to the upper and lower rings at both ends and has an empty space therein; and an inserting rod, which is disposed in the acrylic tube such that its cross section appears on each of the tornograms of the phantom.

7. A phantom for evaluating the accuracy of image registration software based on a result of matching tornograms of a predetermined position of the phantom taken using two or more imaging apparatuses, the phantom comprising:

a container adapted to contain water therein;

a phantom main body installed in the container, the phantom main body having an empty space therein that embodies a portion of the human body, the empty space adapted to container water therein, the phantom main body including a slice stack having a plurality of unit slices stacked in the case and having an empty space therein that embodies the portion of the human body; and at least one indicating bar vertically oriented between the slice stack and an inner sidewall of the container such that its cross section appear in each of the tornograms of the phantom.

8. The phantom of claim 7, wherein the at least one indicating bar comprises:

an acrylic tube, which has an empty space therein; and an inserting rod, which is disposed in the acrylic tube such that its cross section appears on each of the tornograms of the phantom.

9. The phantom of claim 7, wherein the unit slices are plates with a predetermined thickness stacked on a bottom surface of the case, each unit slice includes holes therethrough to allow the unit slice to represent cross sections of the portion of the human body, and the empty space inside the slice stack is defined by the holes in each of the unit slices when the unit slices are stacked.

10. The phantom according to claim 7, wherein the phantom main body has at least one auxiliary hole vertically formed therethrough.

* * * * *